(12) United States Patent
Cheng et al.

(10) Patent No.: US 7,815,883 B2
(45) Date of Patent: Oct. 19, 2010

(54) PREPARATION OF ORGANIC-FUNCTIONALIZED MESOPOROUS SILICA WITH PLATELET MORPHOLOGY AND SHORT MESOCHANNELS

(75) Inventors: Soofin Cheng, Taipei (TW); Shih-Yuan Chen, Taoyuan County (TW); Chin-Chang Chen, Taipei (TW)

(73) Assignee: National Taiwan University, Taipei (TW)

( * ) Notice: Subject to any disclaimer, the term of this patent is extended or adjusted under 35 U.S.C. 154(b) by 182 days.

(21) Appl. No.: 12/343,447

(22) Filed: Dec. 23, 2008

(65) Prior Publication Data

US 2010/0160157 A1    Jun. 24, 2010

(51) Int. Cl.
*C01B 33/12*    (2006.01)

(52) U.S. Cl. ...................... 423/335; 423/324
(58) Field of Classification Search ............ 423/335, 423/324
See application file for complete search history.

(56) References Cited

U.S. PATENT DOCUMENTS

2006/0018966 A1 *    1/2006    Lin et al. .................... 424/484

* cited by examiner

*Primary Examiner*—Timothy C Vanoy
*Assistant Examiner*—Michelle Hou
(74) *Attorney, Agent, or Firm*—CKC & Partners Co., Ltd.

(57) ABSTRACT

A facile synthesis route for preparing SBA-15 silica of platelet shape and very short mesochannels was developed by introducing a small amount of Zr(IV) ions in the first synthesis solution. The synthesis route can be easily extended to prepare SBA-15 materials with various organic functional groups in one pot.

20 Claims, 41 Drawing Sheets

_US 7,815,883 B2_

PREPARATION OF ORGANIC-FUNCTIONALIZED MESOPOROUS SILICA WITH PLATELET MORPHOLOGY AND SHORT MESOCHANNELS

BACKGROUND

1. Field of Invention

The present invention relates to porous silica and a preparation method thereof. More particularly, the present invention relates to mesoporous silica and a preparation method thereof.

2. Description of Related Art

Mesoporous silica materials of high surface areas and well-ordered pore structures have potential applications in separation, catalysis, microelectronic device and enzyme immobilization. SBA-15 material of two-dimensional channeling pores arranged in hexagonal p6mm structure has received great attention because of its relatively large pore and high hydrothermal stability in comparison to MCM-41, its analog in M41S family.

The diameter of the channeling pores of SBA-15 can be varied in 3-10 nm, while the length is usually in the scale of micrometers. Molecular diffusion through the lengthy mesochannels, and pore blockage along the channels are the main concern when applying these materials for sorption and catalysis. Several papers have unveiled the preparation of pure siliceous SBA-15 materials with short mesochannels in the sub-micrometer level by adding either co-surfactant, co-solvent, electrolytes or organosilanes into the first synthesis solutions, but only one of them described the preparation of amino-functionalized mesoporous SBA-15 (Sujandi; Park, S. E.; Han, D. S.; Han, S. C.; Jin, M. J.; Ohsuna, T. _Chem. Commun._ 2006, 4131). Nevertheless, the method was limited to preparing SBA-15 silica with a narrow amino-loading, only in the range of 5-10% in terms of $NH_2$ to $SiO_2$ molar ratio.

SUMMARY

In one aspect, a synthesis method of organic-functionalized mesoporous silica with platelet morphology and short mesochannels is provided below.

First, $EO_{20}PO_{70}EO_{20}$, silicon source, organosilane and Zr(IV) ions are added into a HCl solution to form a synthesis solution. The molar ratio of $EO_{20}PO_{70}EO_{20}$, silicon source, organosilane, Zr(IV) ions, HCl and $H_2O$ is 0.008-0.02:1:0.05-0.3:0.03-0.1:4-12:100-310. The synthesis solution is then hydrothermally heated to form the mesoporous silica. Next, the $EO_{20}PO_{70}EO_{20}$ is removed from the pores of the mesoporous silica by solvent extraction.

According to an embodiment, the silicon source is tetraethyl orthosilicate (TEOS) or sodium silicate.

According to another embodiment, the organosilane is methyltriethoxysilane, phenyltriethoxysilane, (3-chloropropyl)trimethoxysilane, 3-mercaptopropyl-trimethoxysilane, 3-aminopropyltrimethoxysilane, 3-cyanopropyltriethoxysilane, 2-(4-chlorosulfonylphenyl)ethyltrimethoxysilane or carboxyethylsilanetriol sodium salt.

According to yet another embodiment, the Zr(IV) ions are provided by $ZrOCL_2$, $ZrO(NO_3)_2$, and zirconium(IV) acetate hydroxide.

According to yet another embodiment, a salt is additionally added into the HCl solution and the molar ratio of salt/silicon source is not greater than 2.

According to yet another embodiment, the salt is LiCl, LiBr, NaCl, NaBr, KCl, or KBr.

In another aspect, an organic-functionalzied mesoporous silica with platelet morphology and short mesochannels having a length of 100-350 nm synthesized by the synthesis method described above is also provided.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

I. Synthesis of Mesoporous SBA-15 Silica Materials of Platelet Morphology and Short Mesochannels Mesoporous SBA-15 silica materials of platelet morphology and short mesochannels was prepared by dissolving Pluronic P123 triblock copolymer ($EO_{20}PO_{70}EO_{20}$, EO: ethylene oxide, PO: propylene oxide, Aldrich, Mn=5800) in 2M HCl solution at 35° C., followed by adding silicon sources and a small amount of Zr(IV) ions to form a first synthesis solution. The first synthesis solution was sealed in a polypropylene bottle, stirred at 35° C. for 24 h, and then hydrothermally heated at 90° C. under static condition for another 24 h. The solid product was filtered, washed with de-ionized water and dried at 50° C. overnight. The P123 templates were removed by calcining the material at 500° C. in air for 12 h with a ramping rate of 1° C./min.

EXAMPLE 1

Changing the Amounts of Zr(IV) Ions

TABLE 1

| Reactants | Molar ratio |
| --- | --- |
| P123 | 0.017 |
| Si | 1 |
| Zr(IV) | 0.03-0.1 |
| HCl | 7.94 |
| $H_2O$ | 221 |

Various amounts of Zr(IV) ions, as listed in Table 1, are added in the first synthesis solution described above. The silicon source was tetraethyl orthosilicate (TEOS, Acros 98%), and the Zr(IV) source was $ZrOCl_2 \cdot 8H_2O$.

Figure 1A:
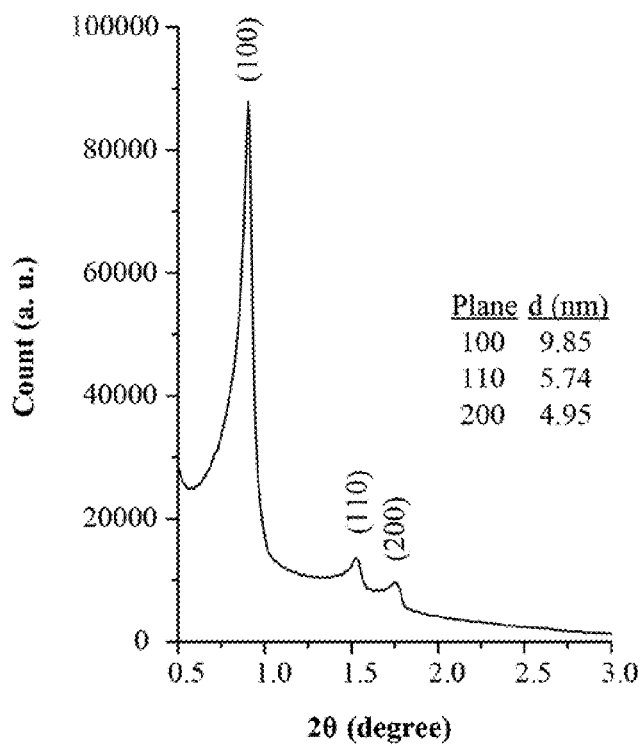
FIG. 1A shows small-angle XRD patterns using Cu $K_\alpha$ radiation source ($\lambda$=1.5418 Å) of the mesoporous SBA-15 silica materials of platelet morphology and short mesochannels.

FIG. 1A shows small-angle XRD patterns using Cu $K_\alpha$ radiation source ($\lambda$=1.5418 Å) of the mesoporous SBA-15 silica materials of platelet morphology and short mesochannels. In FIG. 1A, the resultant materials contain three distinct diffraction peaks at 2θ=0.90, 1.52 and 1.76° indexed to the (100), (110), and (200) planes, respectively, of 2D hexagonal p6mm symmetry.

Figure 1B:
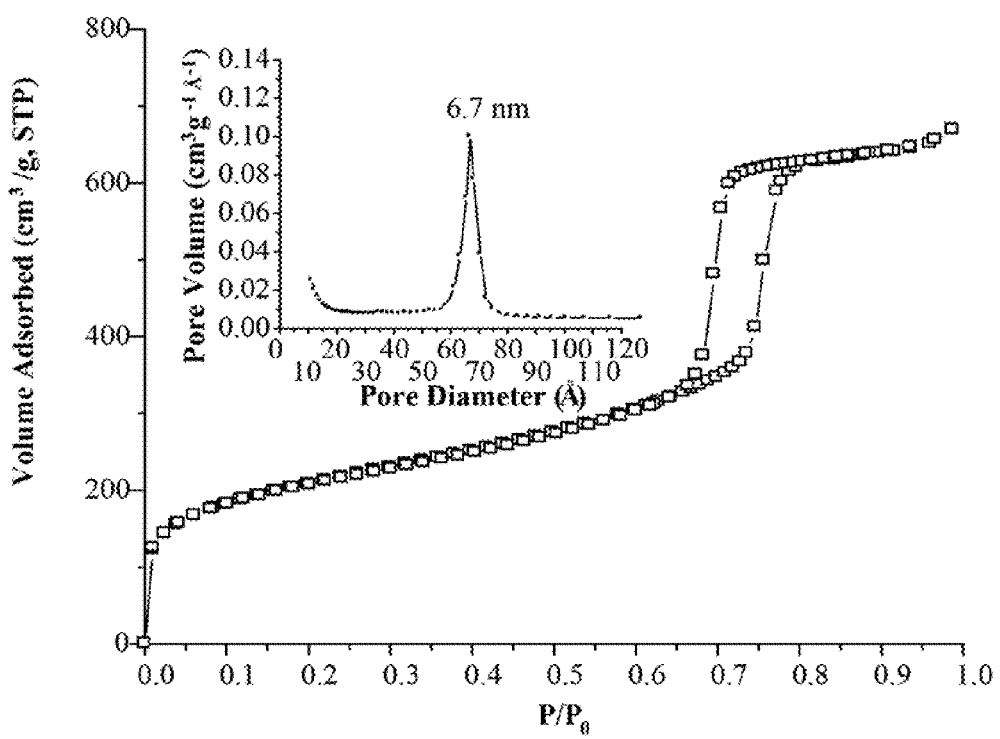
FIG. 1B shows $N_2$ sorption isotherms of the mesoporous SBA-15 silica materials of platelet morphology and short mesochannels.

FIG. 1B shows $N_2$ sorption isotherms of the mesoporous SBA-15 silica materials of platelet morphology and short mesochannels. In FIG. 1B, a narrow pore size distribution with the peak pore diameter at 6.7 nm in the resultant material was shown.

Figure 1C:
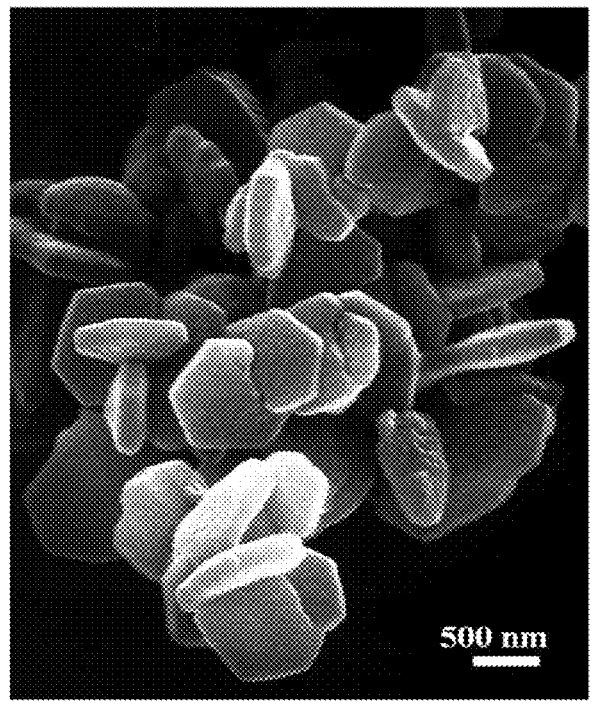
FIG. 1C shows a SEM photograph of the mesoporous SBA-15 silica materials of platelet morphology and short mesochannels.

FIG. 1C shows a SEM photograph of the mesoporous SBA-15 silica materials of platelet morphology and short mesochannels. FIG. 1C shows that the resultant materials were homogeneously dispersed hexagonal thin platelets. The average width and thickness of the platelets are 800-1100 nm and 150-250 nm, respectively.

Figure 1D:
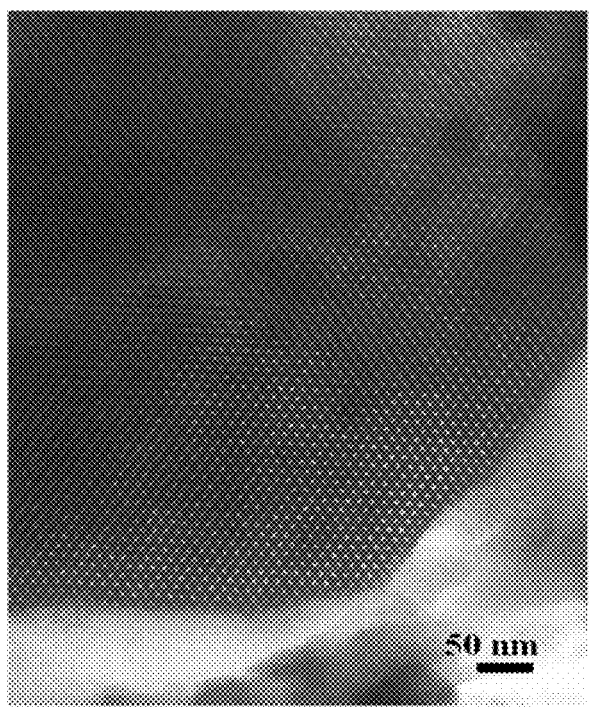
FIG. 1D shows the TEM photographs of the mesoporous SBA-15 silica materials of platelet morphology and short mesochannels.

FIG. 1D shows a TEM photographs of the mesoporous SBA-15 silica materials of platelet morphology and short mesochannels. FIG. 1D shows that the well-ordered pores of the resultant materials were arranged in 2D hexagonal p6mm structure and aligned along the thickness of the thin platelets. In other words, the lengths of mesochannels are the thickness of the thin platelets, which are slightly thinner at the edge and thicker at the center. The platelet morphology and short mesochannels of mesoporous silica materials are quite different from those of conventional mesoporous silica materials, which possess rod or fiber-like morphology and long mesochannels in micrometers.

Based on the SEM and TEM photographs described above, the resultant mesoporous silica materials are similar to conventional mesoporous silica materials of rod-like or fiber-like morphology and long mesochannels in the micrometer level. However, if the Zr/Si ratios are higher then 0.1, the resultant mesoporous silica materials are thin plates or small spheres but the pore structures are poor ordering.

EXAMPLE 2

Changing the Zr(IV) Source

Different zirconium salts, included zirconyl(IV) nitrate hydrate, zirconium(IV) acetate hydroxide, zirconium(IV) acetylacetonate, and zirconium(IV) sulfate tetrahydrate, were used as the Zr(IV) source. The molar ratios of the reactants were the same as those listed in Table 1, and the silicon source was tetraethyl orthosilicate (TEOS, Acros 98%).

Figure 2A:
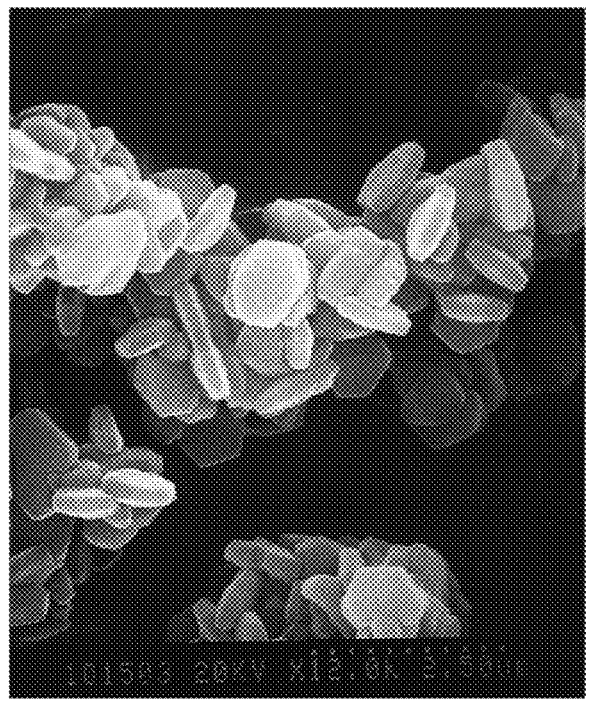
FIGS. 2A-2D shows the SEM photographs of the mesoporous silica materials prepared by using zirconyl(IV) nitrate hydrate, zirconium(IV) acetate hydroxide, zirconium(IV) acetylacetonate, and zirconium(IV) sulfate tetrahydrate, respectively, wherein the Zr/Si ratios were kept at 0.05.
Figure 2B:
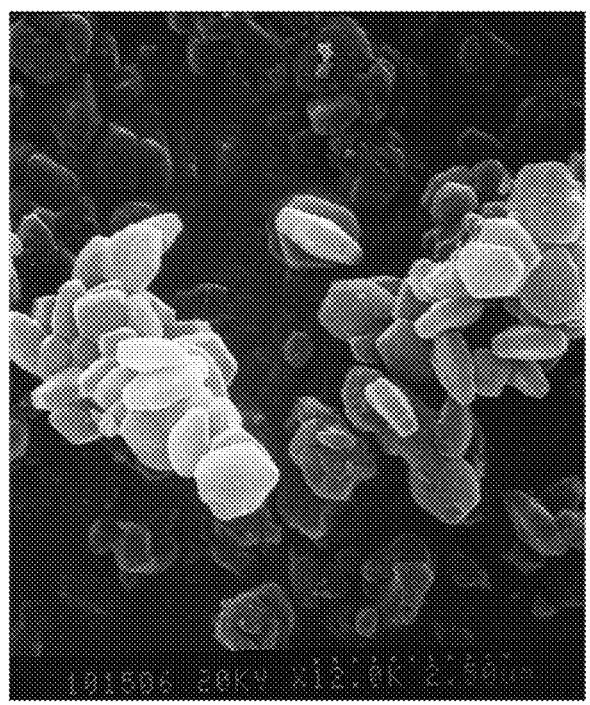

FIGS. 2A-2D shows the SEM photographs of the mesoporous silica materials prepared by using zirconyl(IV) nitrate hydrate, zirconium(IV) acetate hydroxide, zirconium(IV) acetylacetonate, and zirconium(IV) sulfate tetrahydrate, respectively, wherein the Zr/Si ratios were kept at 0.05. In FIGS. 2A and 2B, it demonstrates that the mesoporous silica materials of ordered platelet morphology can be prepared by using $ZrO(NO_3)_2$, and zirconium(IV) acetate hydroxide.

Figure 2C:
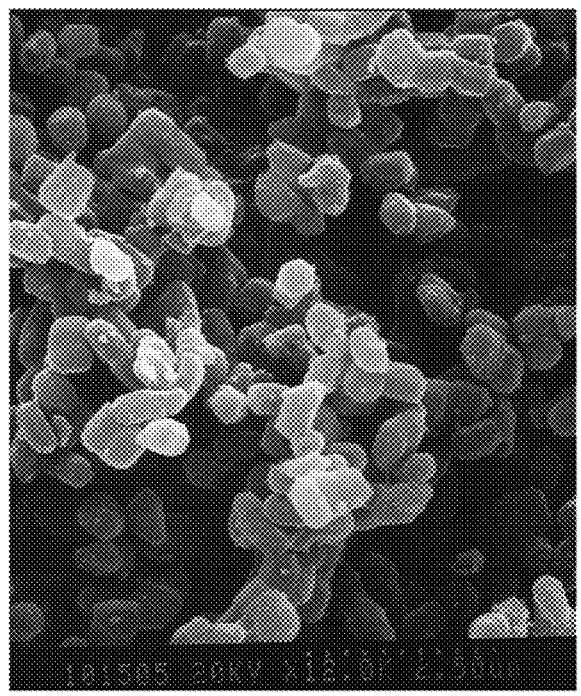
Figure 2D:
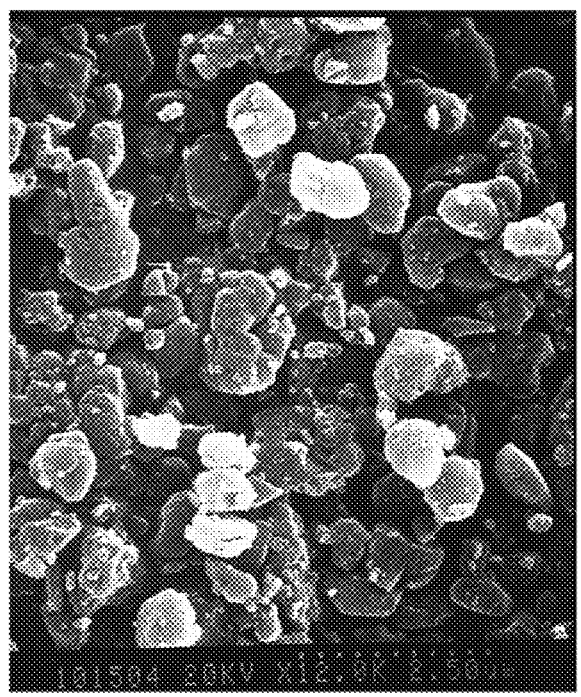

In FIG. 2C, when $Zr(C_5H_7O_2)_4$ was the Zr(IV) source, the material forms short rod-like morphology instead of platelet. In FIG. 2D, when $Zr(SO_4)_2$ was the Zr(IV) source, the platelets are still present but with some holes. Moreover, some irregular pieces of particles can also be seen.

EXAMPLE 3

Changing the Silicon Source

In this example, sodium silicate ($Na_2SiO_3$), instead of TEOS, was used as the silicon source added in the first synthesis solution described above. The molar ratios of the reactants were the same as those listed in Table 1, and the Zr(IV) source was $ZrOCl_2 \cdot 8H_2O$.

Figure 3A:
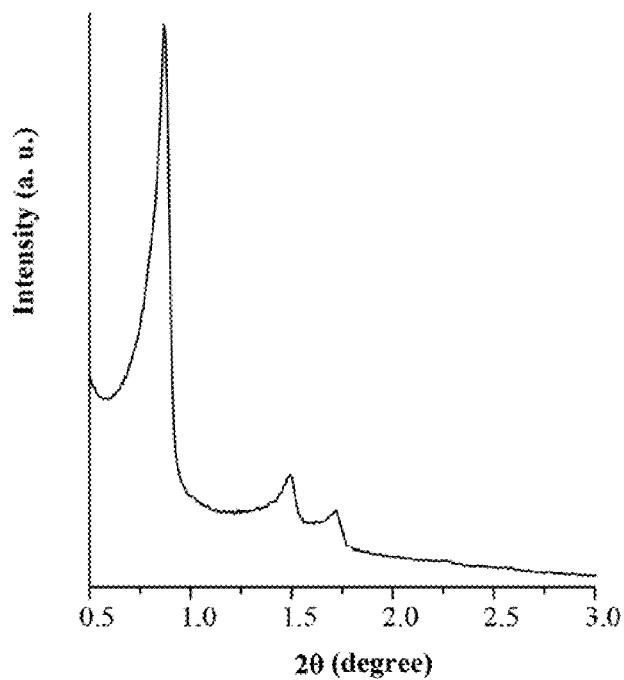
FIG. 3A shows small-angle XRD patterns using Cu $K_\alpha$ radiation source ($\lambda$=1.5418 Å) of siliceous mesoporous material with platelet morphology and short mesochannels prepared by sodium silicate.

FIG. 3A shows small-angle XRD patterns using Cu $K_\alpha$ radiation source (λ=1.5418 Å) of siliceous mesoporous material with platelet morphology and short mesochannels prepared by sodium silicate. It shows that the siliceous mesoporous material prepared by sodium silicate possesses well-ordered 2D hexagonal p6mm pore structure.

Figure 3B:
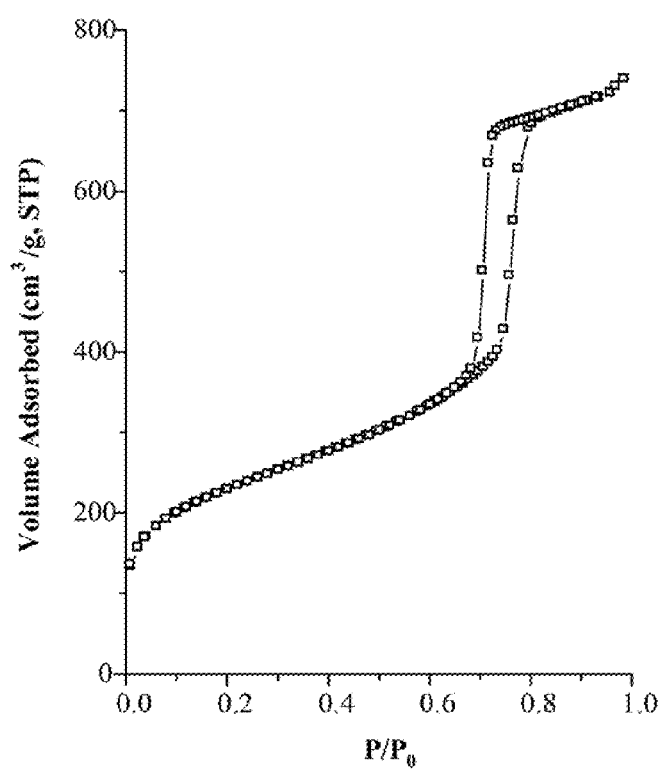
FIG. 3B shows $N_2$ sorption isotherms of siliceous mesoporous material with platelet morphology and short mesochannels prepared by sodium silicate.

FIG. 3B shows $N_2$ sorption isotherms of siliceous mesoporous material with platelet morphology and short mesochannels prepared by sodium silicate. It shows that the siliceous mesoporous material prepared by sodium silicate possesses classical type IV isotherm, similar to conventional mesoporous silica materials, such as MCM-41 and SBA-15 materials.

Figure 3C:
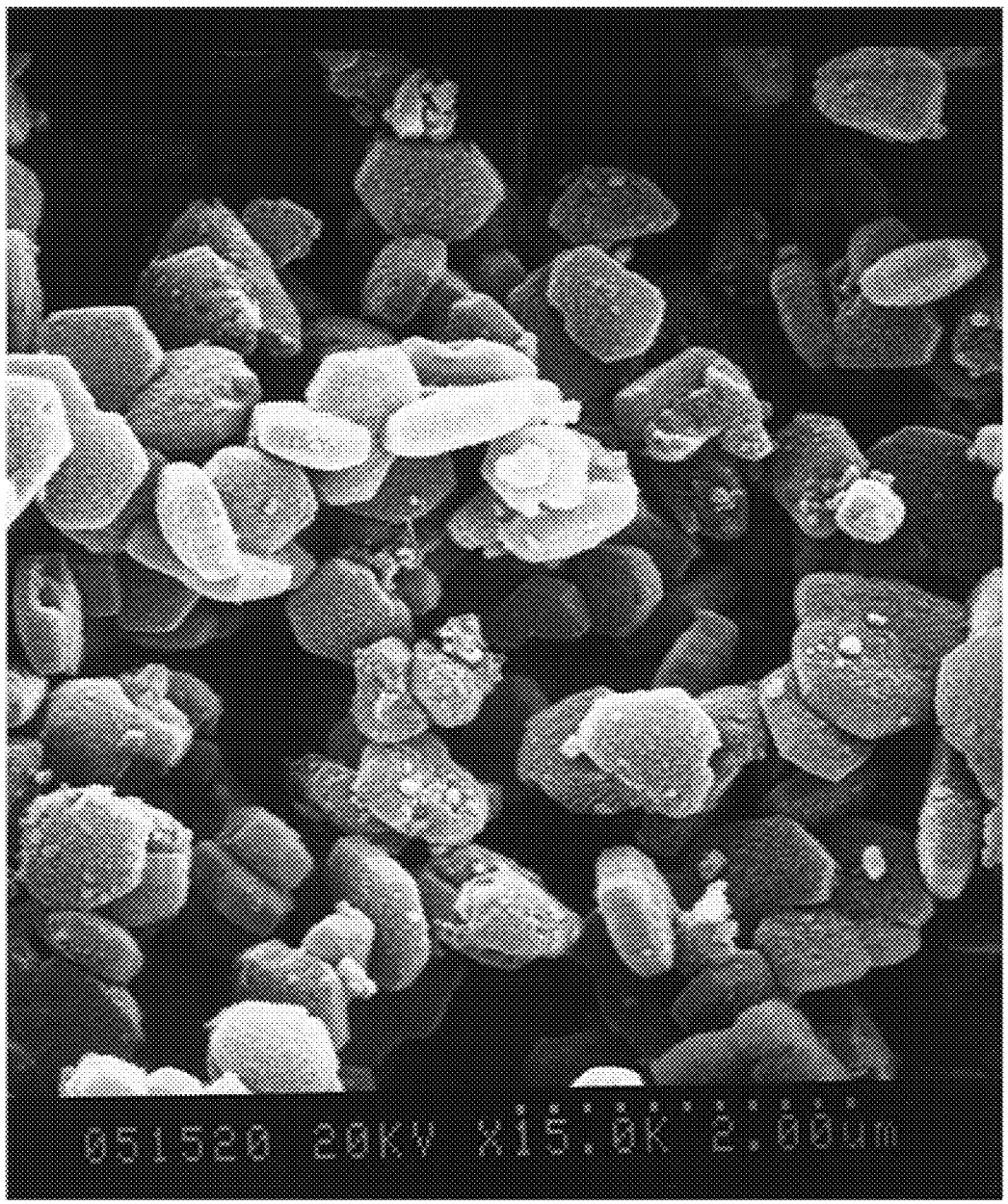
FIG. 3C shows an SEM photograph of siliceous mesoporous material with platelet morphology and short mesochannels prepared by sodium silicate.

FIG. 3C shows an SEM photograph of siliceous mesoporous material with platelet morphology and short mesochannels prepared by sodium silicate. It shows that pure siliceous mesoporous material prepared by sodium silicate has morphology of hexagonal thin plate with 900-1100 nm in width and 150-350 nm in thickness. No significant effect of silicon source (TEOS or sodium silicate) on morphology of mesoporous silica material in this embodiment. It indicates that pure siliceous mesoporous material in this embodiment can be easily prepared by sodium silicate as the silicon source.

EXAMPLE 4

Changing the Amounts of HCl and $H_2O$

TABLE 2

| Reactants | Molar ratio |
| --- | --- |
| P123 | 0.017 |
| Si | 1 |
| Zr(IV) | 0.05 |
| HCl | x = 3.97-11.9 |
| $H_2O$ | y = 102-307 |

Various amounts of HCl and $H_2O$ were added in the first synthesis solution described above. The molar ratios of the reactants are listed in Table 2. The silicon source was tetraethyl orthosilicate (TEOS, Acros 98%), and the Zr(IV) source was $ZrOCl_2 \cdot 8H_2O$.

Figure 4:
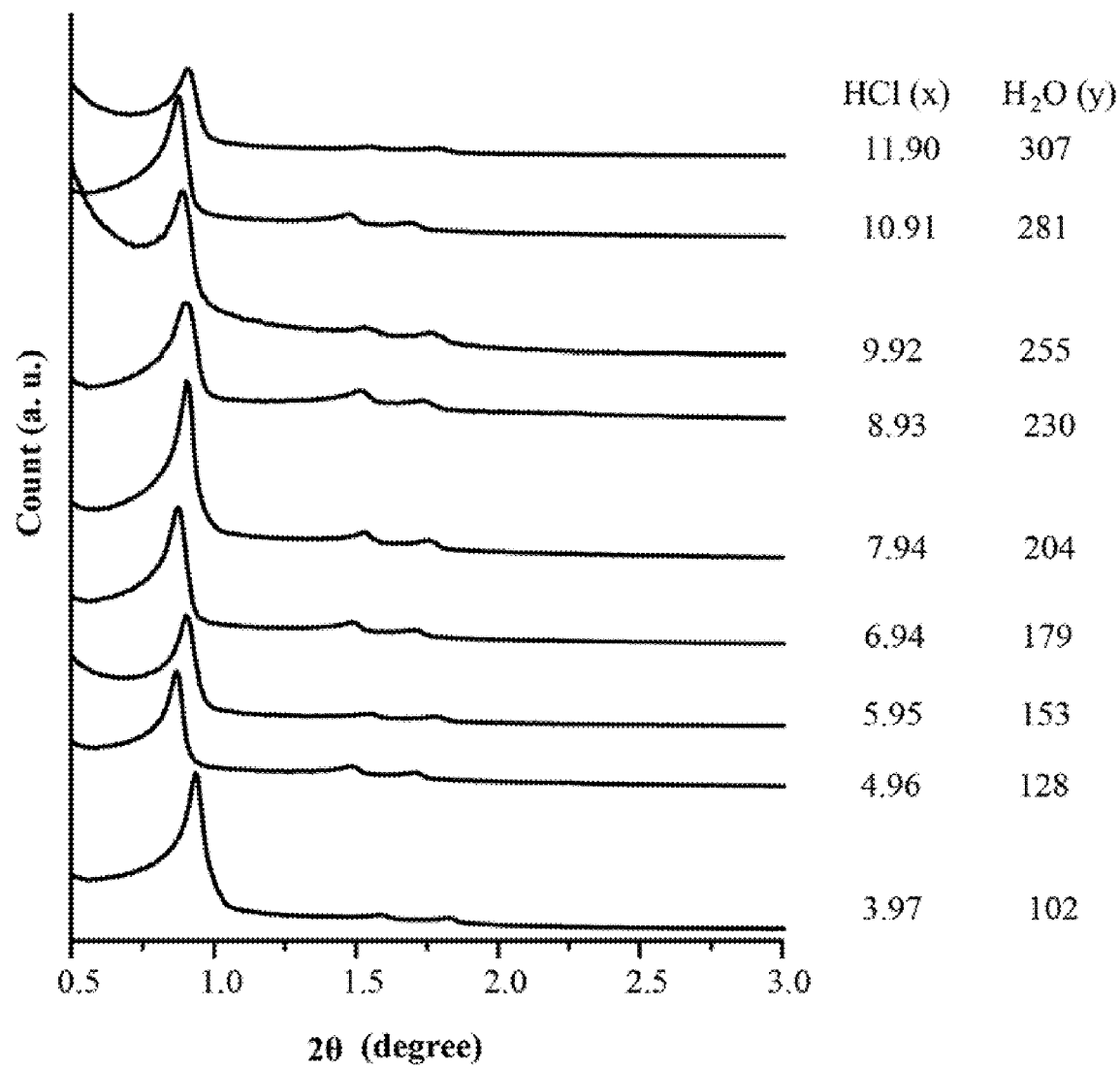
FIG. 4 shows small-angle XRD patterns using Cu $K_\alpha$ radiation source ($\lambda$=1.5418 Å) of siliceous mesoporous silica materials prepared using various amounts of HCl and water solution.
Figure 5A:
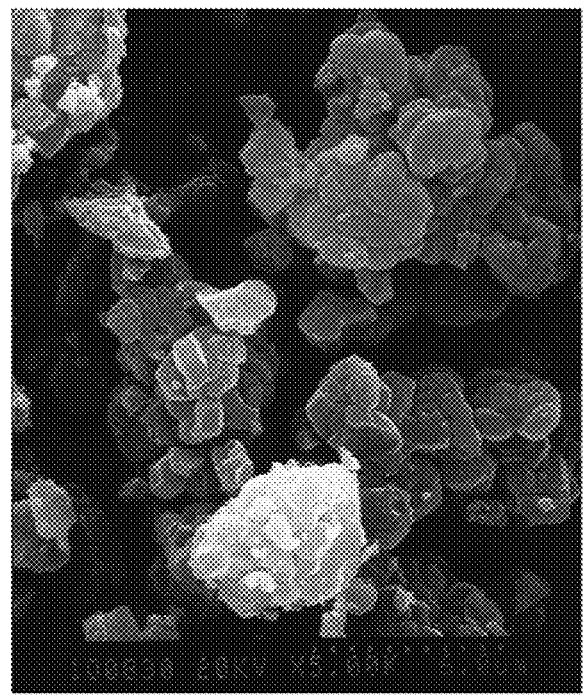
FIGS. 5A-5E shows SEM photographs of siliceous mesoporous silica materials prepared using various amounts of HCl and water solution.
Figure 5B:
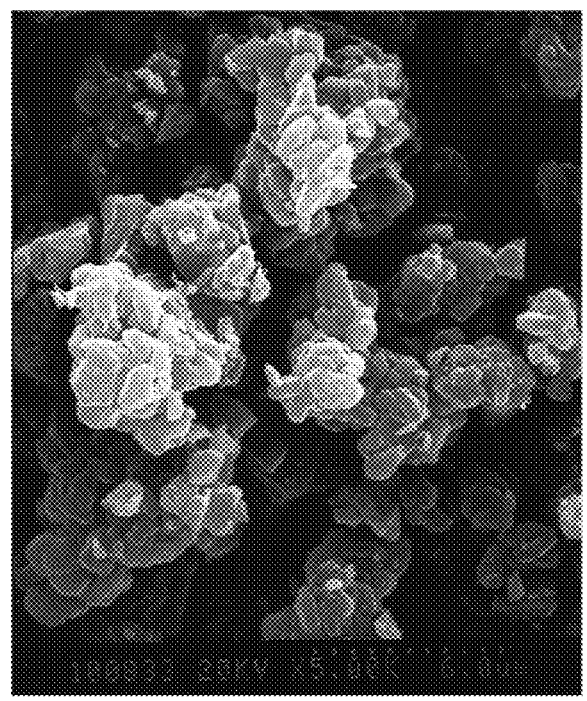
Figure 5C:
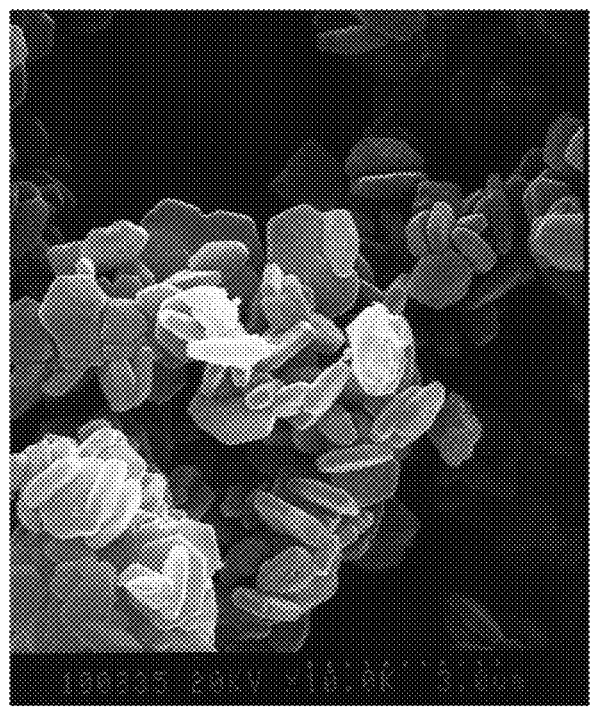
Figure 5D:
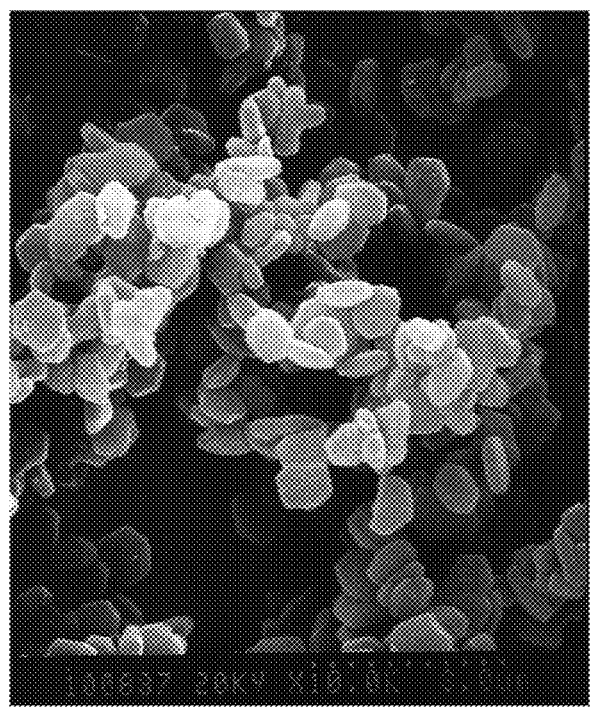
Figure 5E:
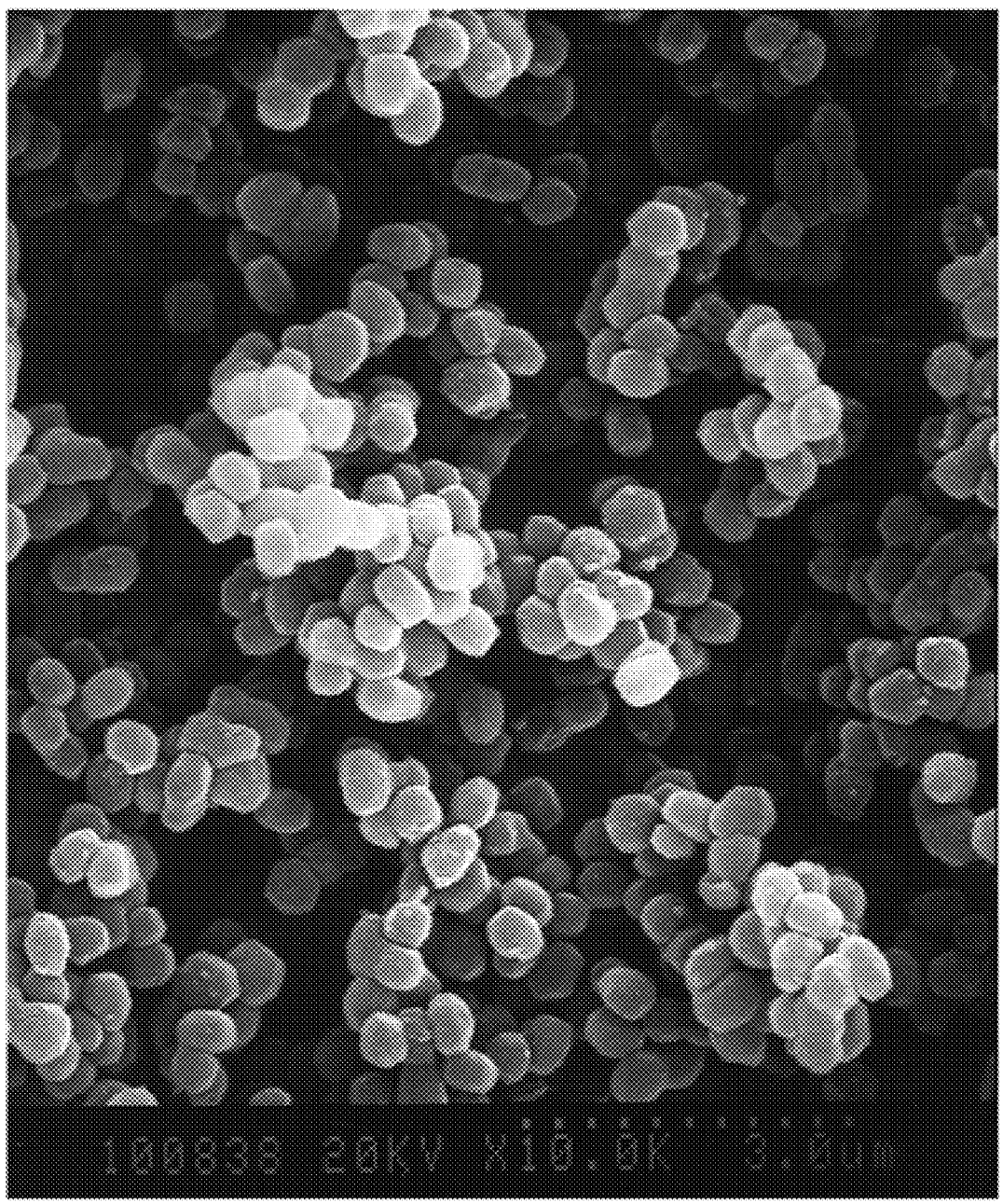

FIG. 4 shows small-angle XRD patterns using Cu $K_\alpha$ radiation source (λ=1.5418 Å) of siliceous mesoporous silica materials prepared using various amounts of HCl and water solution. It shows that all the silica material contains three distinct diffraction peaks indexed to the (100), (110), and (200) planes of 2D hexagonal p6mm symmetry under the present range of HCl and water.

FIGS. 5A-5E shows SEM photographs of siliceous mesoporous silica materials prepared using various amounts of HCl and water solution. The molar ratios of HCl:$H_2O$ were 4.96:128, 5.95:153, 6.94:179, 8.93:230, and 9.92:255 in FIGS. 5A-5E, respectively. The homogeneously dispersed hexagonal thin platelets can be seen in FIGS. 4D-4E, wherein x=6.94-8.93, and y=179-230.

EXAMPLE 5

Changing the Amount of P123 Triblock Copolymer

TABLE 3

| Reactants | Molar ratio |
| --- | --- |
| P123 | x = 0.0043-0.0299 |
| Si | 1 |
| Zr(IV) | 0.05 |

TABLE 3-continued

| Reactants | Molar ratio |
|---|---|
| HCl | 7.94 |
| H$_2$O | 204 |

Various amounts of Pluronic P123 triblock copolymer were added in the first synthesis solution described above. The reactant molar ratios were listed in Table 3. The Zr(IV) source was ZrOCl$_2$.8H$_2$O, and the silicon source was tetraethyl orthosilicate (TEOS, Acros 98%).

Figure 6:
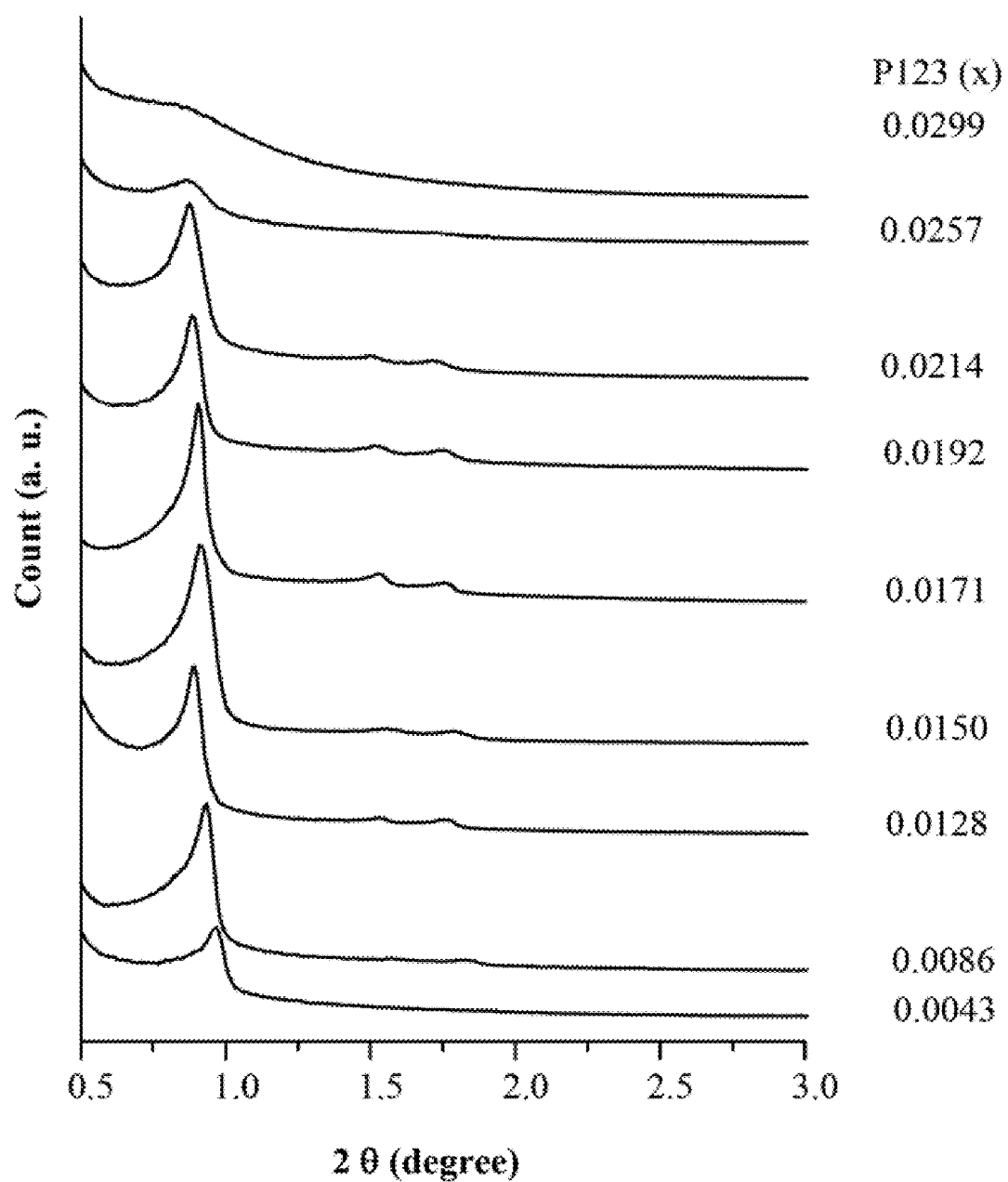
FIG. 6 shows small-angle XRD patterns using Cu $K_\alpha$ radiation source ($\lambda$=1.5418 Å) of siliceous mesoporous silica materials prepared using various amounts of Pluronic P123 triblock copolymer (Aldrich, $M_n$=5800) in 2M HCl solution.
Figure 7A:
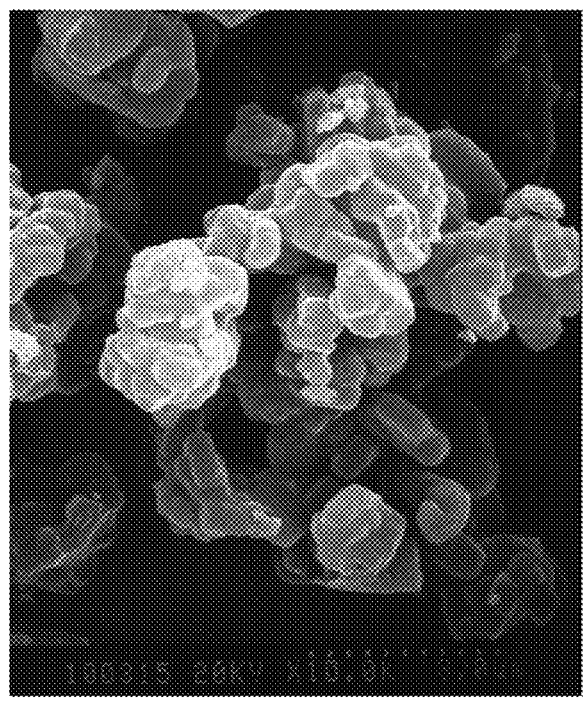
FIGS. 7A-7E show SEM photographs of siliceous mesoporous silica materials prepared using various amounts of Pluronic P123 triblock copolymer (Aldrich, $M_n$=5800) in 2M HCl solution.
Figure 7B:
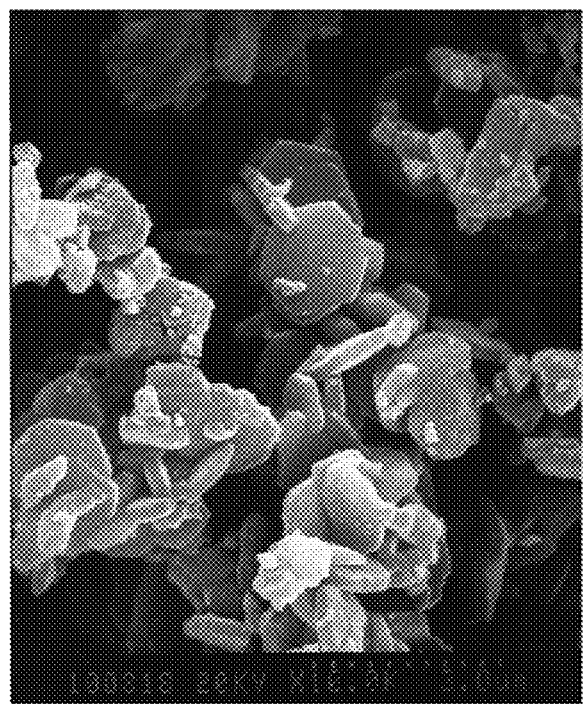
Figure 7C:
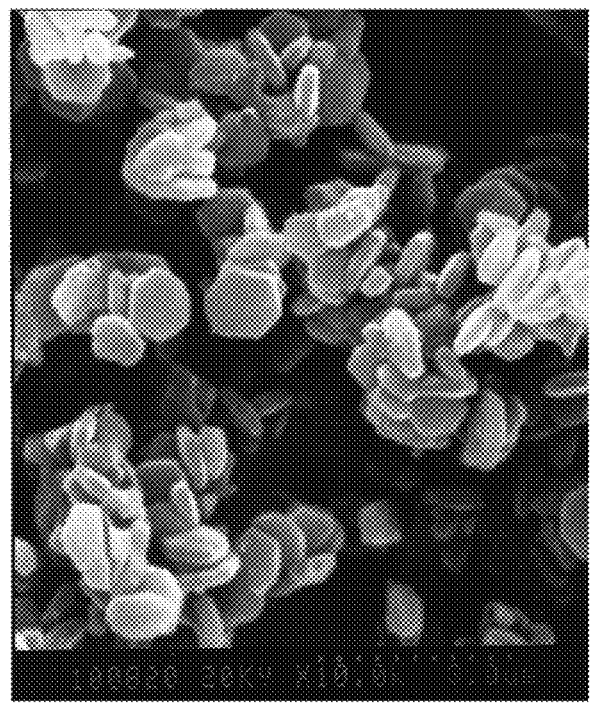
Figure 7D:
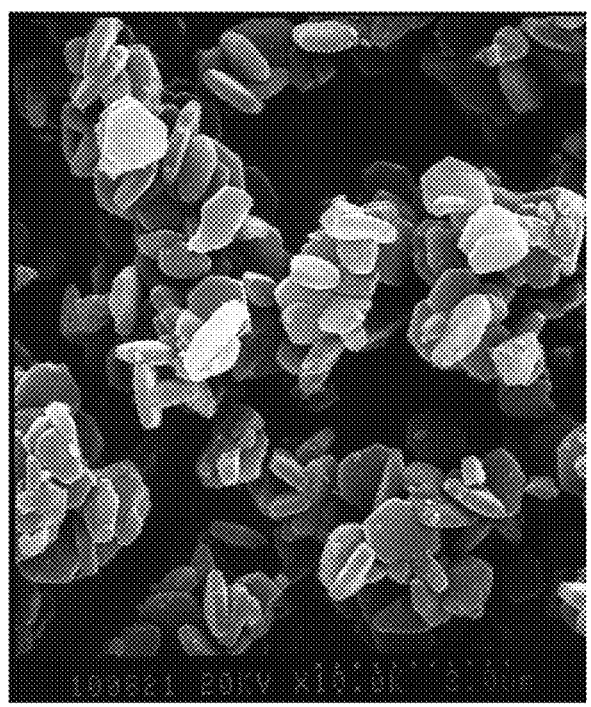
Figure 7E:
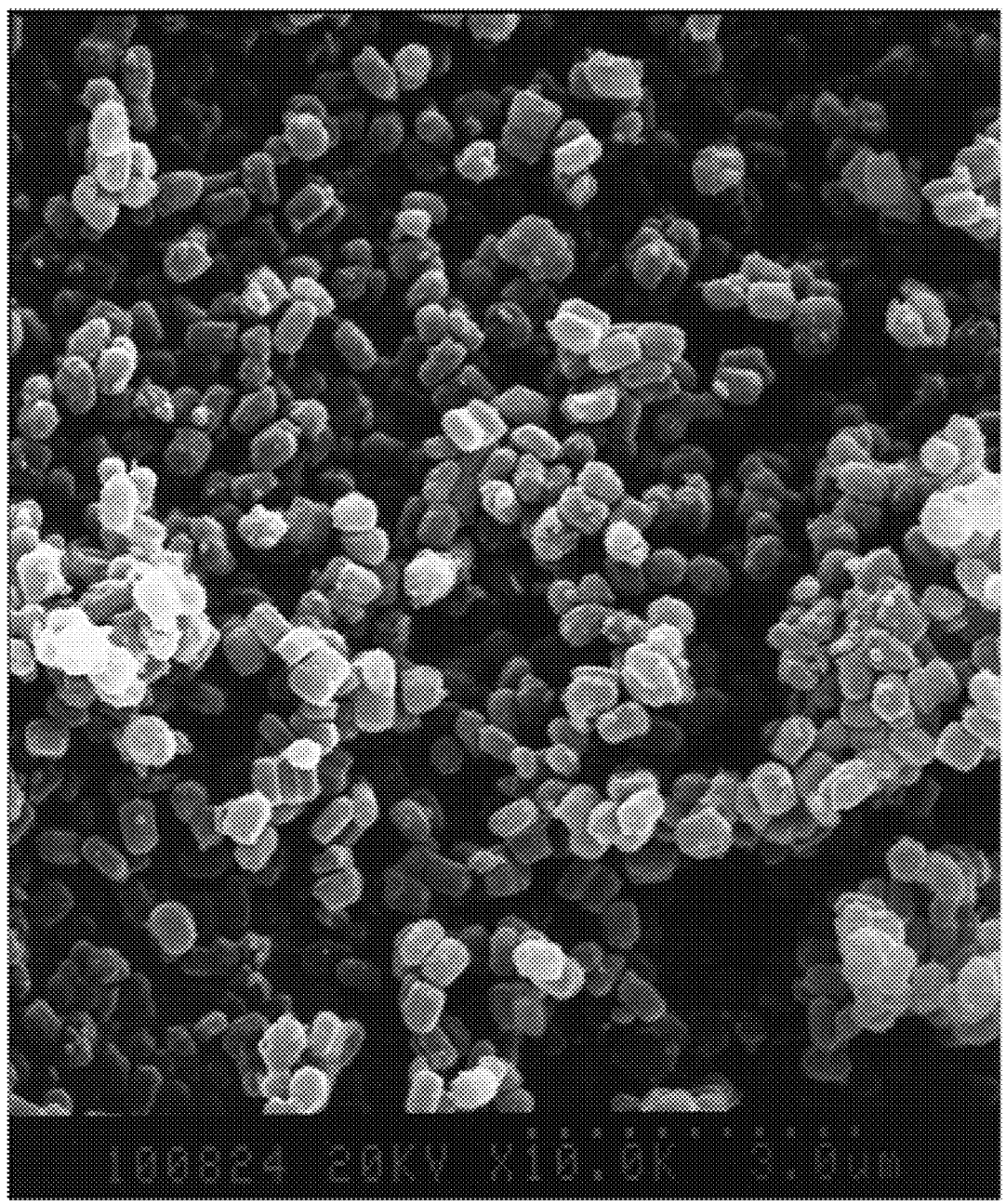
Figure 8A:
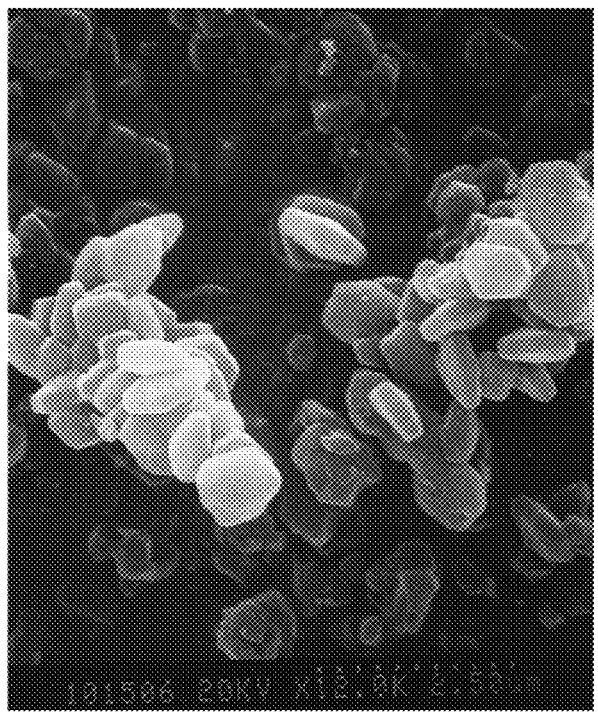
FIGS. 8A-8D show SEM photographs of siliceous mesoporous silica materials prepared by adding various salts into the first synthesis solution.
Figure 8B:
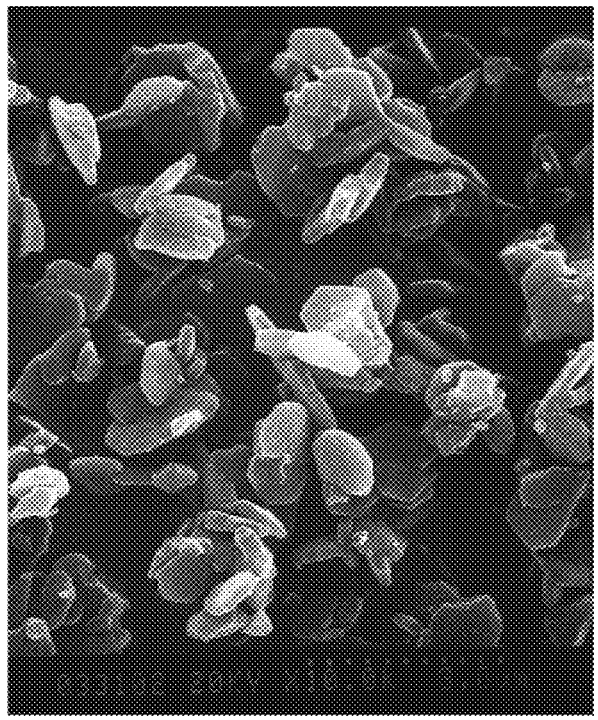
Figure 8C:
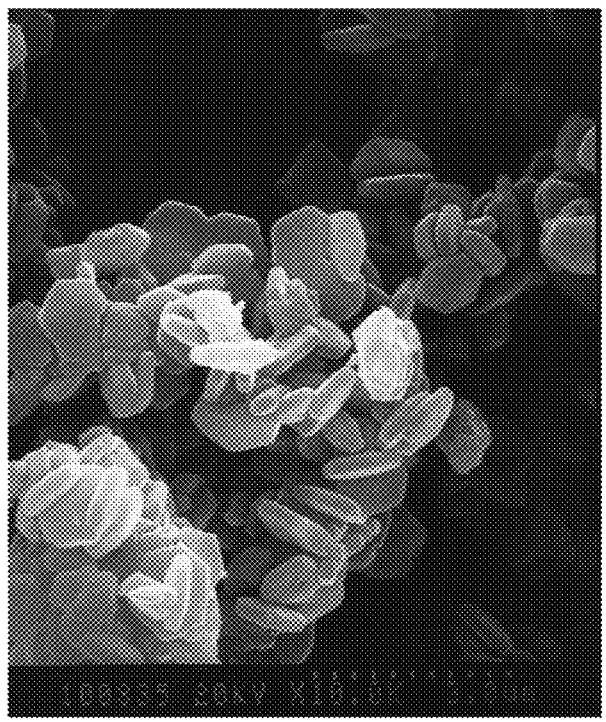
Figure 8D:
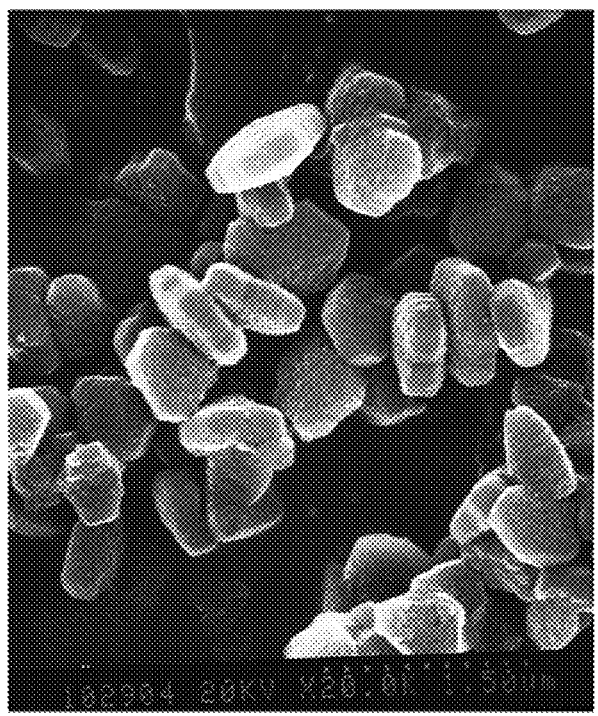

Is FIG. 6 shows small-angle XRD patterns using Cu K$_\alpha$ radiation source ($\lambda$=1.5418 Å) of siliceous mesoporous silica materials prepared using various amounts of Pluronic P123 triblock copolymer (Aldrich, M$_n$=5800) in 2M HCl solution. It shows that mesoporous silica material containing three distinct diffraction peaks indexed to the (100), (110), and (200) planes of 2D hexagonal p6mm symmetry can be seen when x was in the range of 0.0086-0.0214.

FIGS. 7A-7E show SEM photographs of siliceous mesoporous silica materials prepared using various amounts of Pluronic P123 triblock copolymer (Aldrich, M$_n$=5800) in 2M HCl solution. The x values were 0.0086, 0.0128, 0.015, 0.0192, and 0.214 in FIGS. 7A-7E, respectively. The homogeneously dispersed hexagonal thin platelets are obtained when x was 0.0128-0.0192.

EXAMPLE 6

Adding Additional Salts

TABLE 4

| Reactants | Molar ratio |
|---|---|
| P123 | 0.017 |
| Si | 1 |
| Zr(IV) | 0.05 |
| HCl | 7.94 |
| H$_2$O | 221 |
| Salt | 0-2 |

Various salts were additionally added in the first synthesis solution. The salt can be LiCl, LiBr, NaCl, NaBr, KCl, or KBr, for example. The reactant molar ratios are listed in Table 4. The Zr(IV) source was ZrOCl$_2$.8H$_2$O, and the silicon source was tetraethyl orthosilicate (TEOS, Acros 98%).

FIGS. 8A-8D show SEM photographs of siliceous mesoporous silica is materials prepared by adding various salts into the first synthesis solution. The molar ratio of salt was kept at 2. The salts used were LiCl, NaCl, NaBr, or KCl in FIGS. 8A-8D, respectively. The homogeneously dispersed hexagonal thin platelets are obtained when any of the above mentioned salts were added.

II. Synthesis of Functionalized Mesoporous SBA-15 Silica Materials of Platelet Morphology and Short Mesochannels—Without Prehydrolysis The synthesis route is extended to prepare organic-functionalized mesoporous silica materials with platelet morphology and short mesochannels by co-condensation of TEOS and organosilane in the conventional synthesis solution of mesoporous silica materials with adding Zr(IV) ions. The synthesis method is described as below.

Organic functionalized mesoporous SBA-15 silica materials of platelet morphology and short mesochannels were prepared by dissolving Pluronic P123 triblock copolymer (Aldrich, Mn=5800) in HCl solution at 35° C., followed by adding TEOS (or sodium silicate) and organosilane as the silicon source and adding a small amount of Zr(IV) ions to form a second synthesis solution. The second synthesis solution was sealed in a polypropylene bottle, stirred at 35° C. for 24 h, and then hydrothermally heated at 90° C. under static condition for is another 24 h. The solid product was filtered, washed with de-ionized water and dried at 50° C. overnight. The P123 templates were removed by ethanol extraction at 78° C. for 1 day.

EXAMPLE 7

Synthesis of Organic-Functionalized Mesoporous Silica Materials with Functional Groups of CH$_3$—, Ph-, Cl(CH$_2$)$_3$—, SH(CH$_2$)$_3$— or CN(CH$_2$)$_3$—

TABLE 5

| Reactants | Molar ratio |
|---|---|
| P123 | 0.017 |
| TEOS | 1 |
| Organic silane | 0.05-0.3 |
| Zr(IV) | 0.03-0.1 |
| HCl | 7.94 |
| H$_2$O | 221 |

The platelet organic-functionalized mesoporous silica materials with short mesochannels are prepared. The reactant molar ratios are listed in Table 5. The organic silane can be methyltriethoxysilane, phenyltriethoxysilane, (3-chloropropyl)trimethoxysilane, 3-mercaptopropyltrimethoxysilane, 3-cyanopropyltriethoxysilane, 2-(4-chlorosulfonylphenyl)ethyltrimethoxysilane, or carboxyethylsilanetriol sodium salt, for example. The Zr(IV) source was ZrOCl$_2$.8H$_2$O.

Figure 9A:
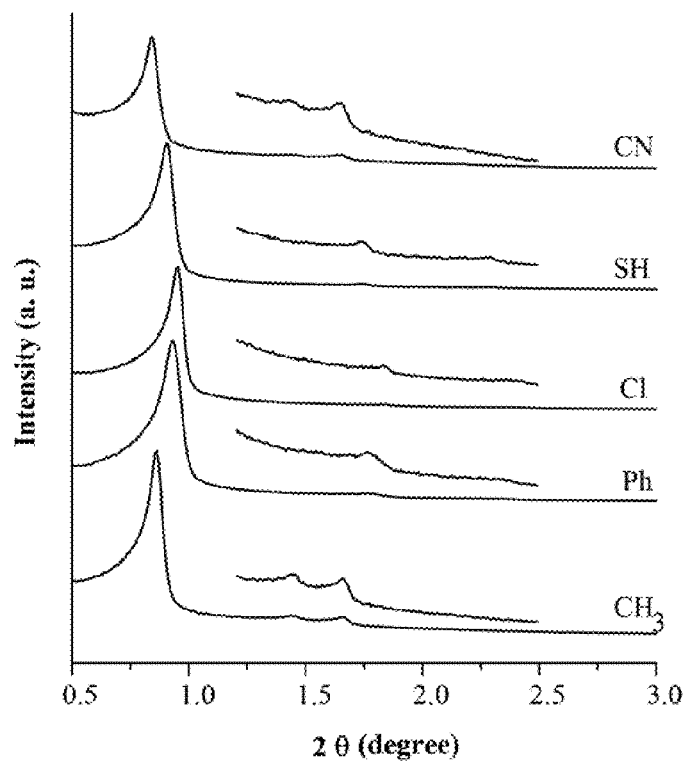
FIG. 9A shows small-angle XRD patterns using Cu $K\alpha$ radiation source ($\lambda$=1.5418 Å) of the resultant mesoporous silica materials with various organic functionalities.

FIG. 9A shows small-angle XRD patterns using Cu Kα radiation source ($\lambda$=1.5418 Å) of the resultant mesoporous silica materials with various organic functionalities (briefly termed FG), including CH$_3$—, Ph-, Cl(CH$_2$)$_3$—, SH(CH$_2$)$_3$— and CN(CH$_2$)$_3$— groups. All materials show three distinct diffraction peaks indexed to the (100), (110), and (200) planes of 2D hexagonal p6mm symmetry.

Figure 9B:
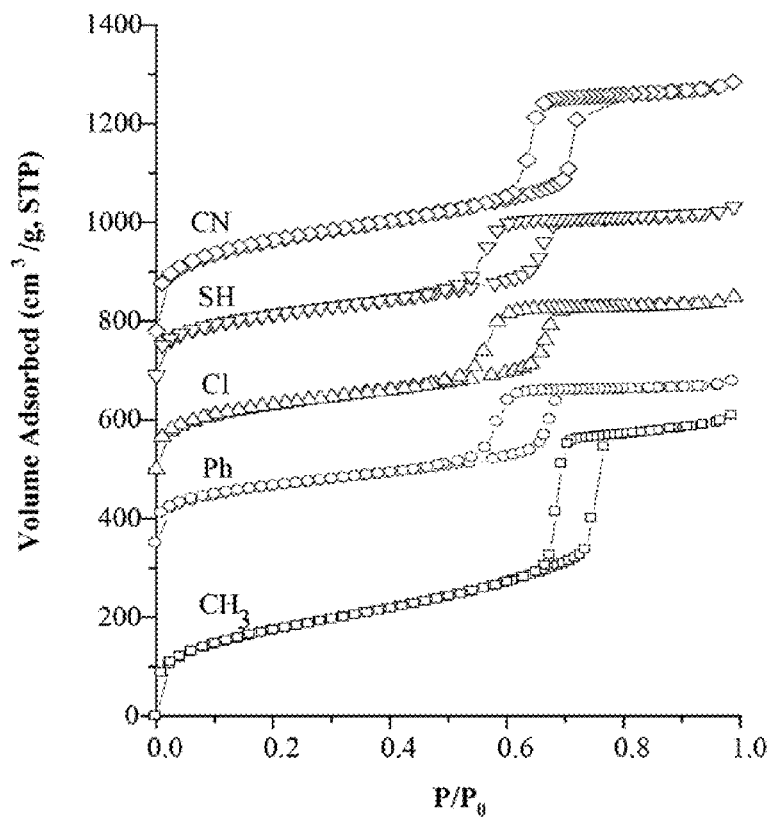
FIG. 9B shows the $N_2$ sorption isotherms of the ethanol extracted platelet mesoporous silica materials.
Figure 10A:
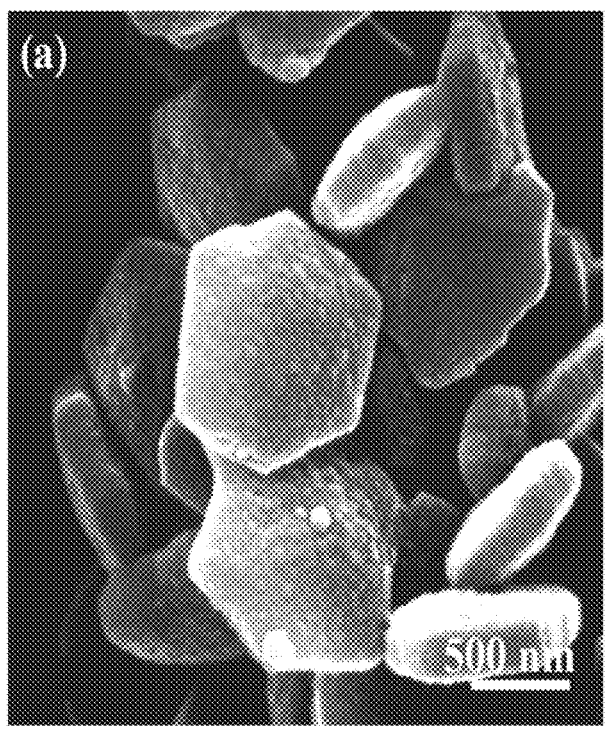
FIGS. 10A-10E show SEM images of the resultant mesoporous silica materials with various organic functionalities.
Figure 10B:
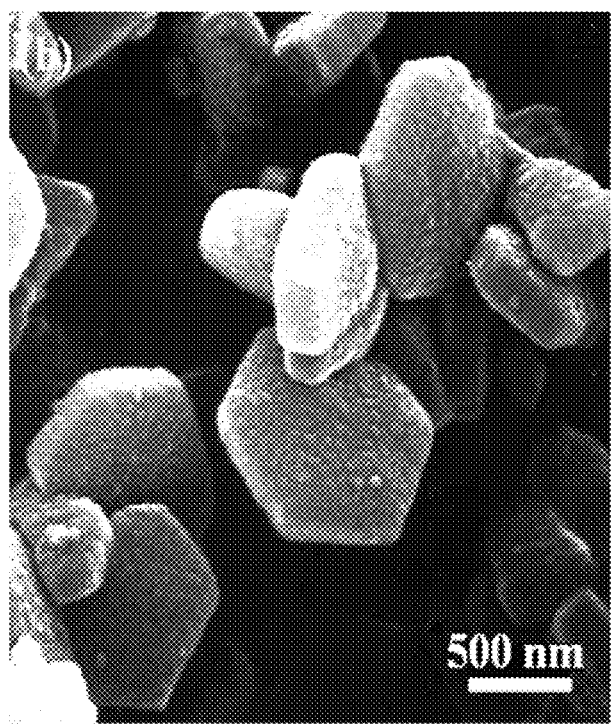
Figure 10C:
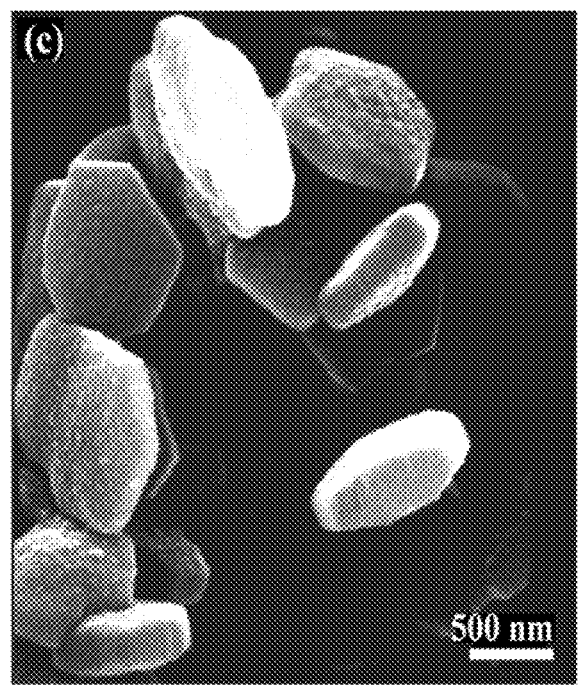
Figure 10D:
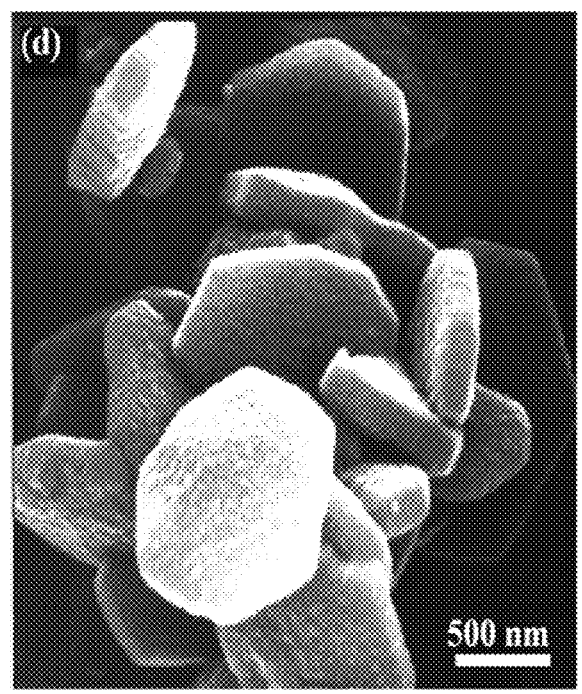
Figure 10E:
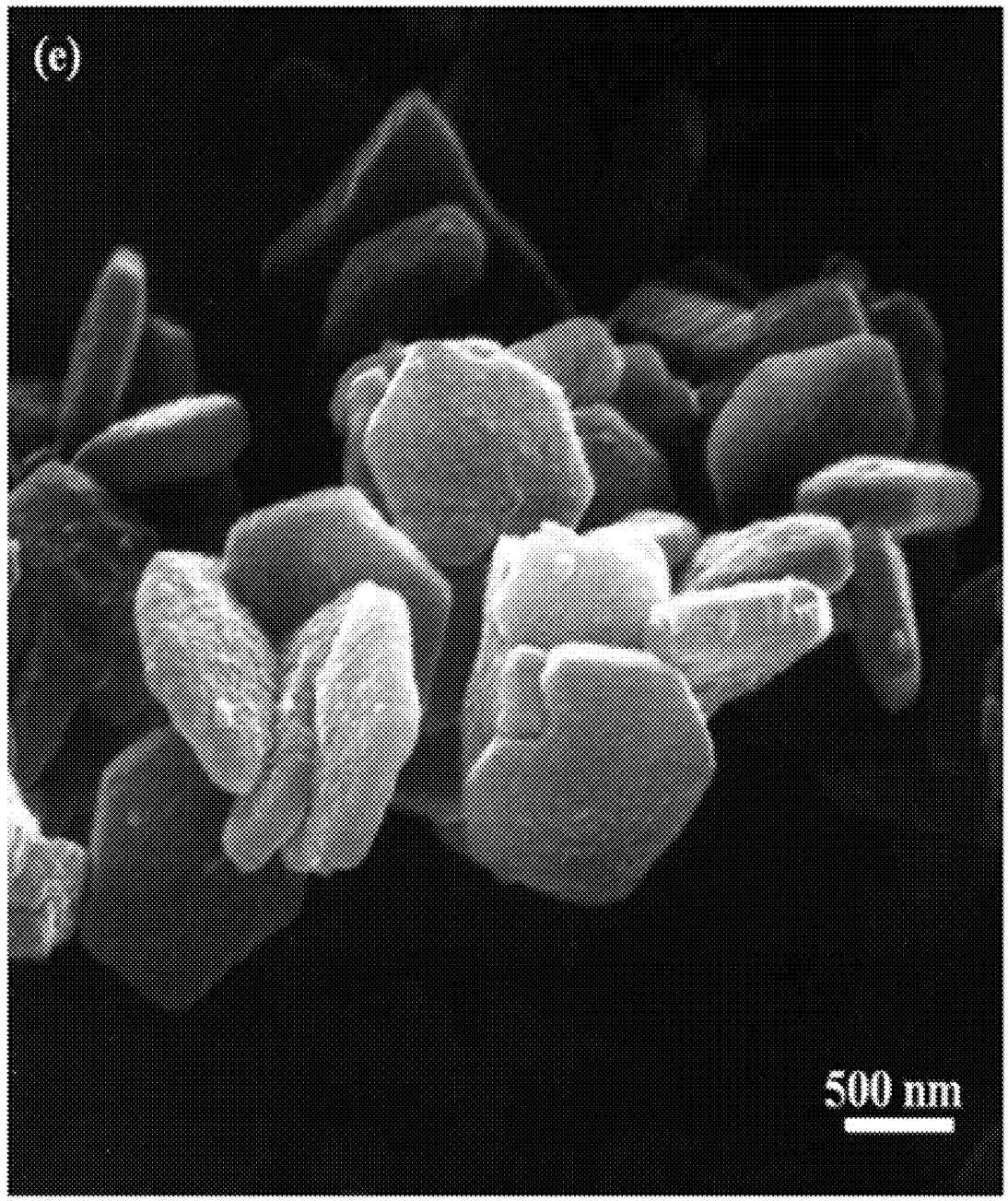
Figure 11A:
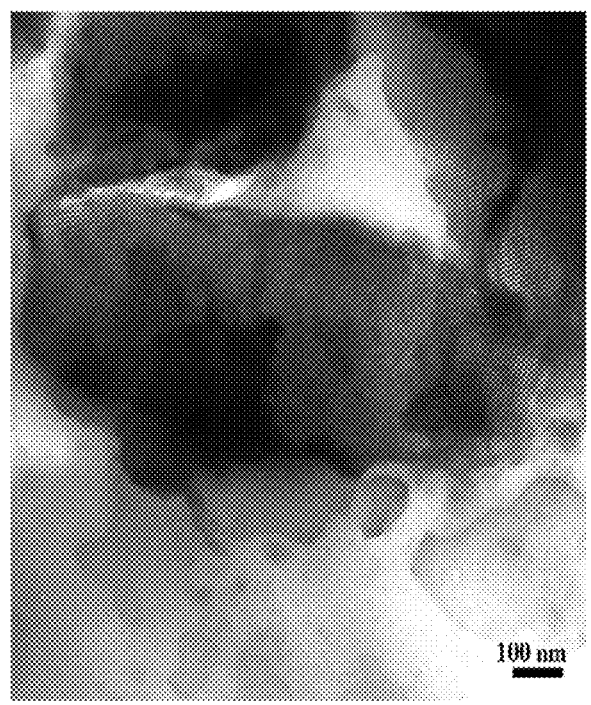
FIGS. 11A-11E shows TEM images of the resultant mesoporous silica materials with various organic functionalities.
Figure 11B:
Figure 11C:
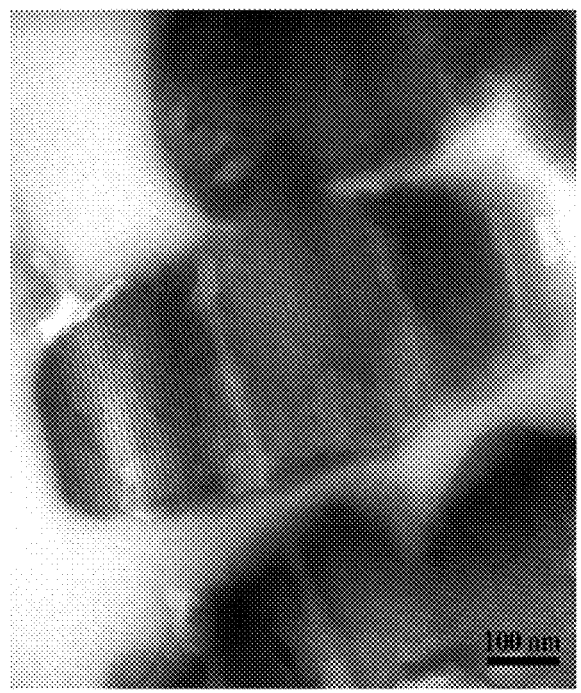
Figure 11D:
Figure 11E:

FIG. 9B shows the N$_2$ sorption isotherms of the ethanol extracted platelet mesoporous silica materials. It show the classical type IV isotherms with H1 hysteresis loops appeared at P/P$_0$ at about 0.5 to about 0.8, depending on the functional groups. All materials possess high surface area (611-810 m$^2$/g), large pore volume (0.57-1.01 cm$^3$/g), thick pore wall (4.6-7.1 nm) and large mesopores (4.2-6.7 nm) with narrow pore size distribution (PSD<1.4 nm), similar to those of conventional mesoporous silica materials. BJH analyses of the N$_2$ sorption isotherms showed that the platelet organic-functionalized mesoporous silica materials have smaller pore sizes but thicker pore walls than those of mesoporous SBA-15 materials.

Moreover, the elemental analyses indicate that the FG/Si molar ratios in the solid products are similar to those introduced in the synthesis solutions. These results described above infer that most of the organosilane precursors were incorporated onto the silica framework.

FIGS. 10A-10E show SEM images of the resultant mesoporous silica materials with various organic functionalities, including CH$_3$—, Ph-, Cl(CH$_2$)$_3$—, SH(CH$_2$)$_3$—, and CN(CH$_2$)$_3$— groups, respectively. FIGS. 11A-11E shows TEM images of the resultant mesoporous silica materials with various organic functionalities, including $CH_3$—, Ph-, $Cl(CH_2)_3$—, $SH(CH_2)_3$—, and $CN(CH_2)_3$— groups, respectively.

The SEM and TEM photographs shown in FIGS. 10 and 11 indicated that all the materials are still homogeneously dispersed hexagonal thin platelets.

The thickness of the platelets of the functionalized mesoporous silica materials is slightly thicker than that of pure siliceous mesoporous SBA-15 materials, but is the channeling pores are still aligned along the height of the platelets. The average thickness of the platelets is within 150-350 nm.

Figure 12A:
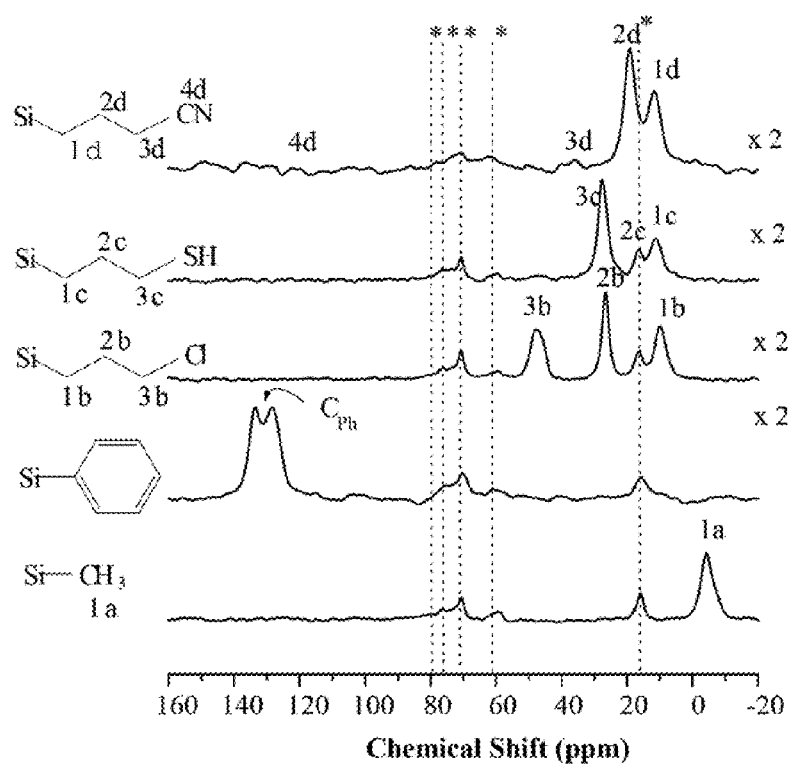
FIG. 12A shows solid state $^{13}C$ CP-MAS spectra of various extracted organic-functionalized, including $CH_3$—, Ph-, $Cl(CH_2)_3$—, $SH(CH_2)_3$— and $CN(CH_2)_3$— groups, mesoporous silica materials with platelet morphology and short mesochannels.

FIG. 12A shows solid state $^{13}C$ CP-MAS spectra of various extracted organic-functionalized, including $CH_3$—, Ph-, $Cl(CH_2)_3$—, $SH(CH_2)_3$— and $CN(CH_2)_3$— groups, mesoporous silica materials with platelet morphology and short mesochannels. Peaks labeled * corresponding to carbon atoms from the P123 residue. In the $^{13}C$ CP-MAS NMR spectra, the peak at −4.2 ppm corresponds to the C atom on the $CH_3$—Si group, two peaks at 128.2 and 133.7 ppm correspond to C atoms on the ph-Si groups, and three distinct peaks appeared at 9.6-11.7, 16.4-26.5 and 27.7-47.6 ppm corresponding to the carbon atoms of Si—$CH_2$—$CH_2$—$CH_2$— groups in sequence from left to right for the propylene-containing functional groups. Additional weak peaks at 24, 71, 74 and 76 ppm are attributed to the residual P123 template in the material. The $^{13}C$ NMR spectra confirmed that the platelet mesoporous silica materials are indeed incorporated with various organic functional groups and the organic moieties are not decomposed during the preparation procedures.

Figure 12B:
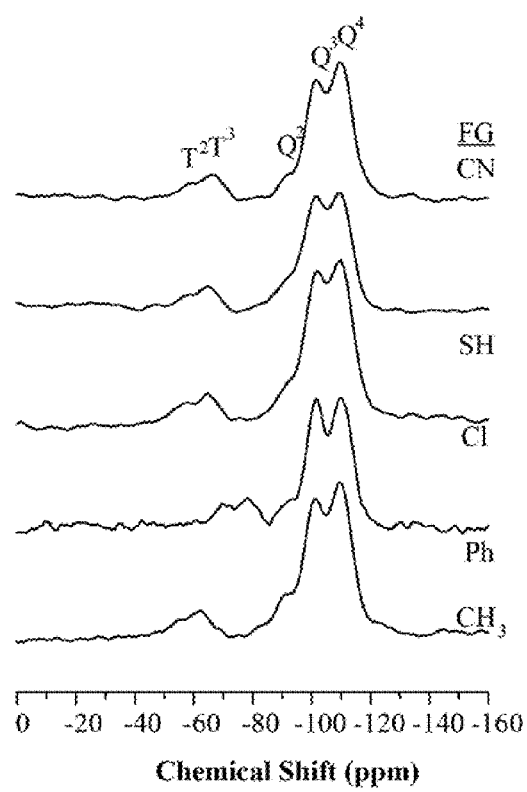
FIG. 12B shows solid state $^{29}Si$ MAS NMR spectra of various extracted organic-functionalized, including $CH_3$—, Ph-, $Cl(CH_2)_3$—, $SH(CH_2)_3$— and $CN(CH_2)_3$— groups, mesoporous silica materials with platelet morphology and short mesochannels.

FIG. 12B shows solid state $^{29}Si$ MAS NMR spectra of various extracted organic-functionalized, including $CH_3$—, Ph-, $Cl(CH_2)_3$—, $SH(CH_2)_3$— and $CN(CH_2)_3$— groups, mesoporous silica materials with platelet morphology and short mesochannels. The $^{29}Si$ MAS NMR spectra of the functionalized mesoporous silica platelets all have three distinct resonance peaks in up-field corresponding to $Q^n$ ($Q^n$=Si$(OSi)_n(OH)_{4-n}$, n=2-4; $Q^4$ at δ=−110 ppm, $Q^3$ at δ=−101 ppm, and $Q^2$ at δ=−91 ppm) and three weaker peaks in downfield assigned to $T^m$ ($T^m$=RSi$(OSi)_m(OH)_{3-m}$, m=1-3). The appearance of $T^m$ peaks confirms that the organic silane is incorporated as a part of the silica wall structure. The $\Sigma T^m/\Sigma Q^n$ values are around 0.086-0.097, which are in consistence with the results of elemental analyses. It indicates that most of organic functionalities is incorporated into the frameworks of mesoporous silica materials.

EXAMPLE 8

Synthesis of —$(CH_2)_3SO_3H$ Functionalized Mesoporous Silica Materials with Platelet Morphology and Short Mesochannels

TABLE 6

| Reactants | Molar ratio |
|---|---|
| P123 | 0.017 |
| TEOS | 1 |
| MPTMS* | 0.05-0.3 |
| Zr(IV) | 0.03-0.1 |
| HCl | 7.94 |
| $H_2O_2$ | 0.4-3 |
| $H_2O$ | 221 |

*MPTMS: 3-mercaptopropyltrimethoxysilane

In this example, the —$(CH_2)_3SO_3H$ functionalized mesoporous silica materials with platelet morphology and short mesochannels was synthesized. The reactant molar ratios are listed in Table 6. The Zr(IV) source was $ZrOCl_2.8H_2O$. The MPTMS was in-situ oxidized by $H_2O_2$ to form —$(CH_2)_3SO_3H$ functional group.

Figure 13A:
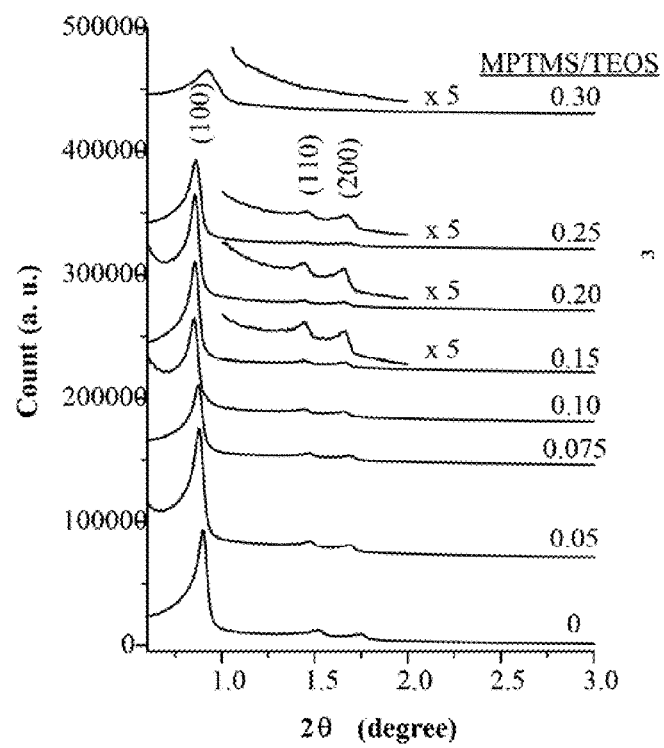
FIG. 13A shows small-angle XRD patterns of extracted propylsulfonic acid-functionalized mesoporous silica materials with platelet morphology and various MPTMS/TEOS ratios.
Figure 16A:
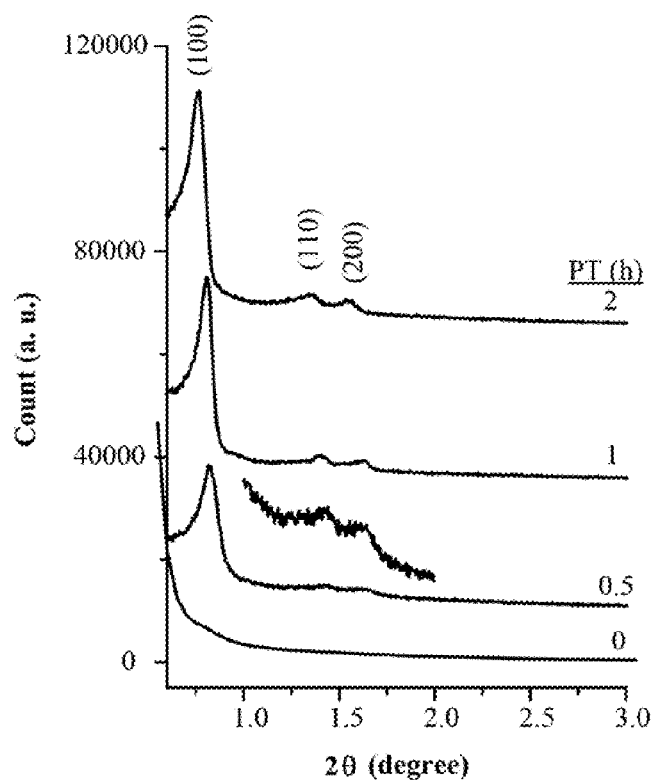
FIG. 16A shows small-angle XRD patterns of aminopropyl-functionalized mesoporous silica materials prepared with various TEOS pre-hydrolysis (PT) times.

FIG. 13A shows small-angle XRD patterns of extracted propylsulfonic acid-functionalized mesoporous silica materials with platelet morphology and various MPTMS/TEOS ratios. As shown in FIG. 16A, the (100), (110) and (200) diffraction planes of 2D hexagonal p6mm symmetry are found when propylsulfonic acid-functionalized mesoporous silica materials are prepared by MPTMS/TEOS ratios within 0.05-0.25. By further increasing the MPTMS/TEOS ratio to 0.30, the XRD pattern of resultant material showed one broad and weak diffraction peak.

Figure 13B:
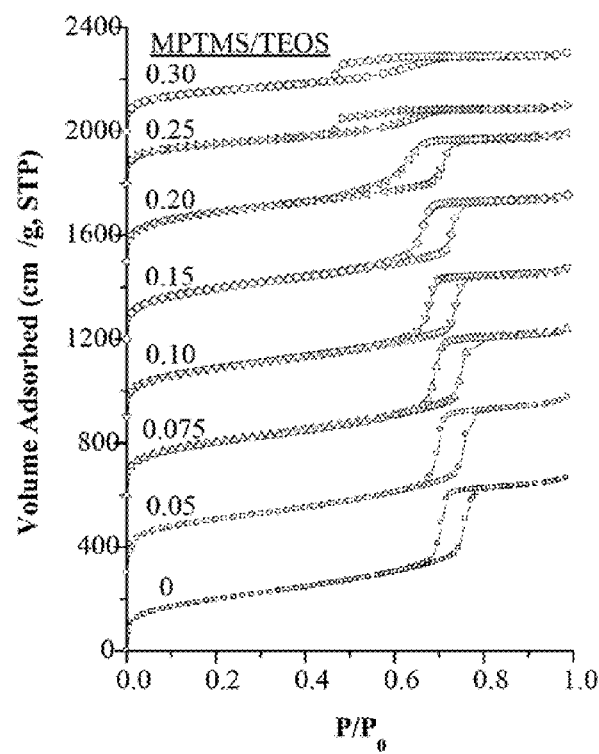
FIG. 13B shows $N_2$ adsorption-desorption isotherms of extracted propylsulfonic acid-functionalized mesoporous silica materials with platelet morphology and various MPTMS/TEOS ratios.
Figure 14A:
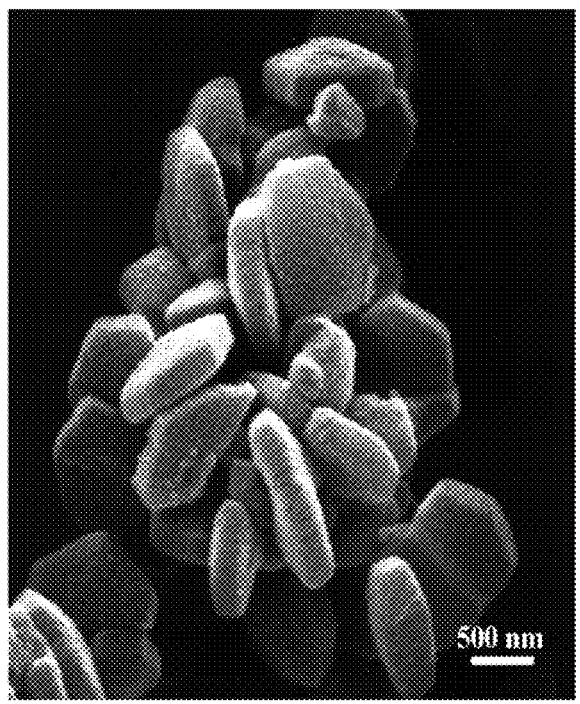
FIGS. 14A-14F shows SEM and selected TEM photographs of extracted propylsulfonic acid-functionalized mesoporous silica materials with platelet morphology and various MPTMS/TEOS ratios of 0.05, 0.15, 0.20, 0.30, 0.10, and 0.10, respectively.
Figure 14B:
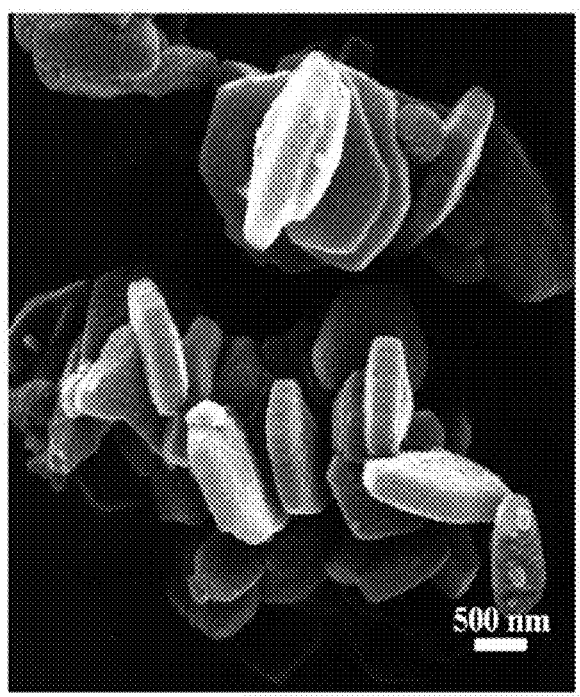
Figure 14C:
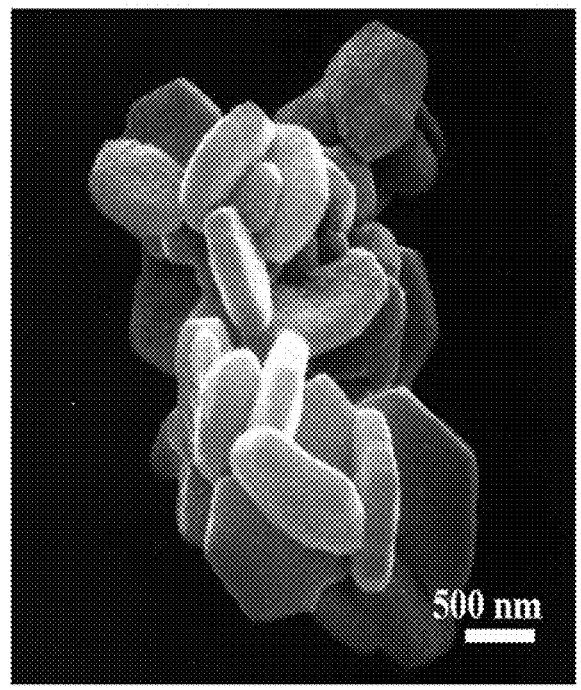
Figure 14D:
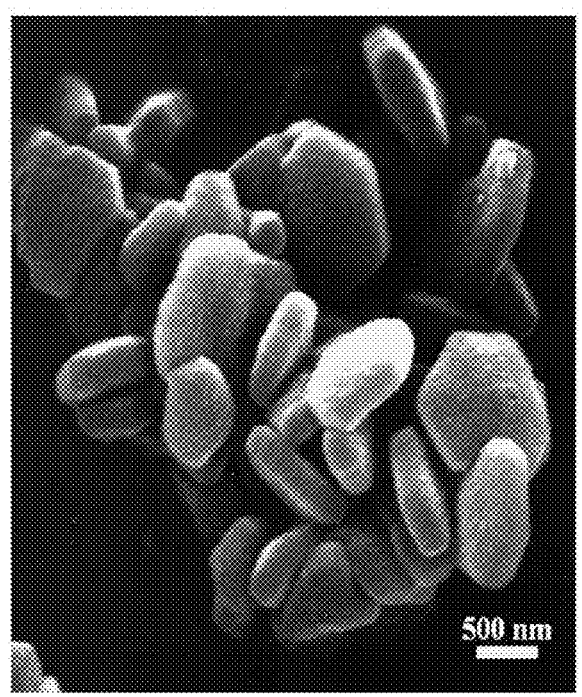
Figure 14E:
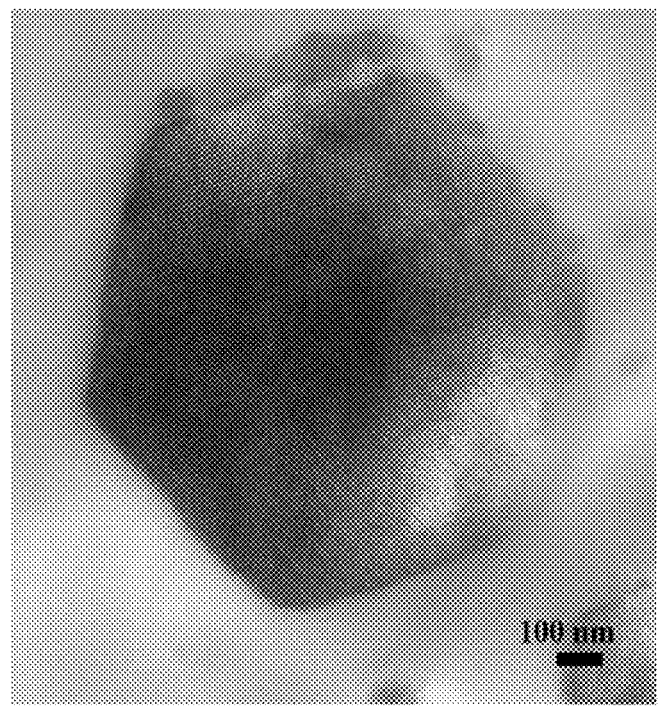
Figure 14F:
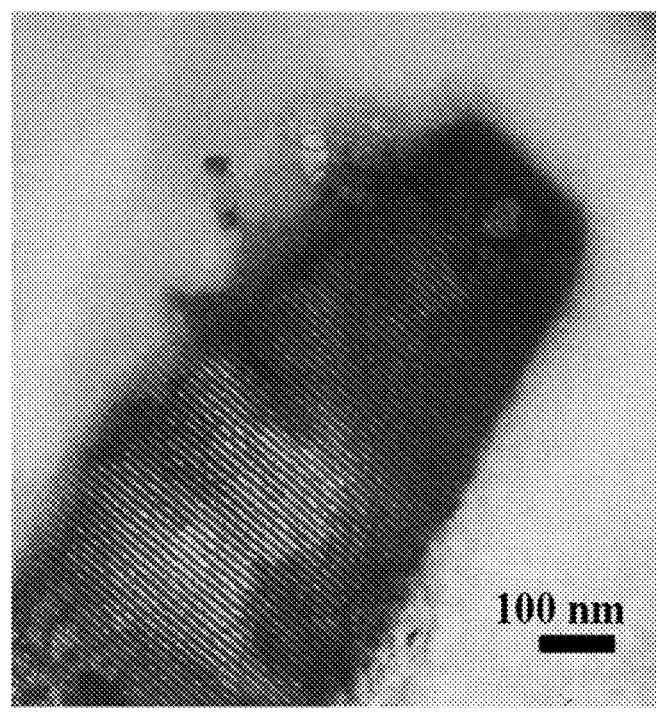

FIG. 13B shows $N_2$ adsorption-desorption isotherms of extracted propylsulfonic acid-functionalized mesoporous silica materials with platelet morphology and various MPTMS/TEOS ratios. $N_2$ adsorption-desorption isotherms and pore size distributions indicate that large mesoporous structure with narrow PSD was present in the propylsulfonic acid-functionalized mesoporous silica materials prepared with MPTMS/TEOS ratios of 0.05-0.25. With a MPTMS/TEOS ratio of 0.30, $N_2$ physisorption shows a characteristic type IV isotherm with a $H_2$ hysteresis loop presented in the material, implying that the cage-like pore structure was present.

FIGS. 14A-14F shows SEM and selected TEM photographs of extracted propylsulfonic acid-functionalized mesoporous silica materials with platelet morphology and various MPTMS/TEOS ratios of 0.05, 0.15, 0.20, 0.30, 0.10, and 0.10, respectively. In FIG. 14, SEM and TEM photographs show that all propylsulfonic acid-functionalized mesoporous silica materials with MPTMS/TEOS molar ratios varied in 0.05-0.3 are platelet morphology and short mesochannels, which are not significantly affected by the propylsulfonic acid loadings.

Figure 15A:
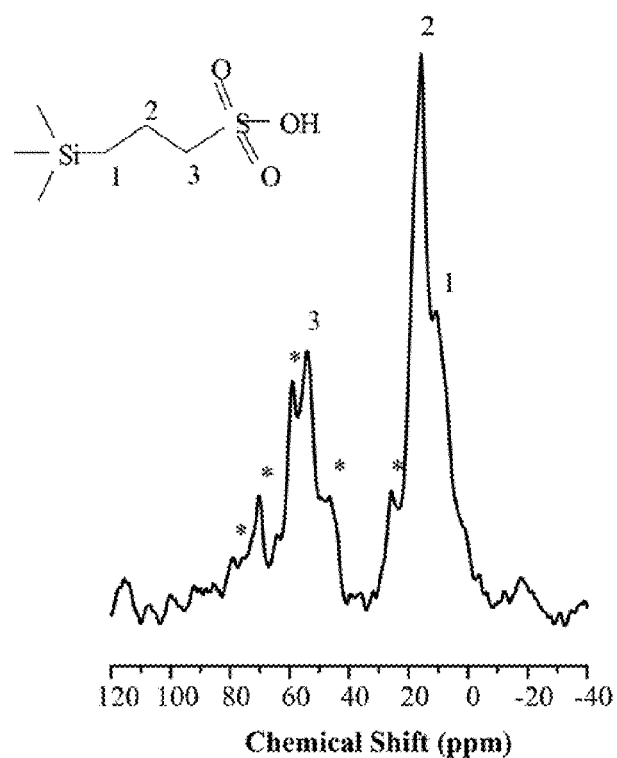
FIG. 15A shows solid state $^{13}C$ CP-MAS spectra of propylsulfonic acid-functionalized mesoporous silica materials with platelet morphology and short mesochannels.

FIG. 15A shows solid state $^{13}C$ CP-MAS spectra of propylsulfonic acid-functionalized mesoporous silica materials with platelet morphology and short mesochannels. Peaks labeled * corresponding to carbon atoms from the P123 residue. In FIG. 15A, $^{13}C$ CP-MAS NMR spectrum shows that three distinct peaks centered at 10.7, 15.8 and 54.0 ppm, corresponding to the carbon atoms on the ≡Si—$CH_2$—$CH_2$—$CH_2$—$SO_3H$ group in the sequence from left to right, could be clearly observed.

Figure 15B:
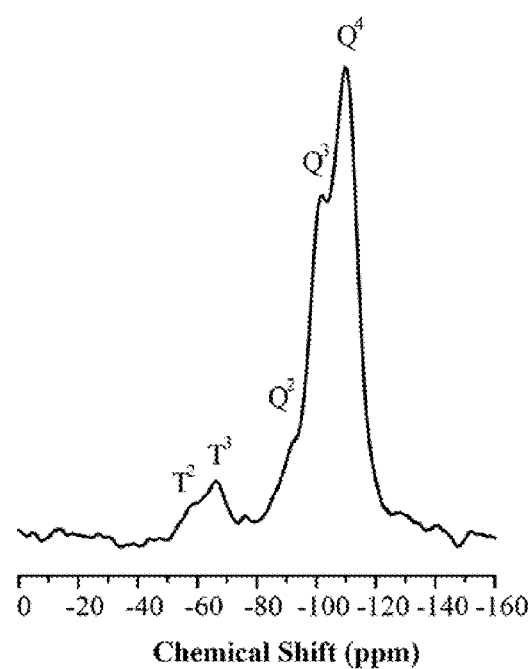
FIG. 15B shows $^{29}Si$ MAS NMR spectra of propylsulfonic acid-functionalized mesoporous silica materials with platelet morphology and short mesochannels.

FIG. 15B shows $^{29}Si$ MAS NMR spectra of propylsulfonic acid-functionalized mesoporous silica materials with platelet morphology and short mesochannels. In FIG. 15B, three distinct resonance peaks with chemical shifts of −92, −101, −110 ppm were indexed to $Q^2$, $Q^3$ and $Q^4$ bands corresponding to the siloxanes species of $Si(OSi)_2(OH)_2$, $Si(OSi)_3(OH)$ and $Si(OSi)_4$. Another two resonance peaks were observed at −59 and −66 ppm, which were indexed to $T^2$ and $T^3$ bands corresponding to the organosiloxane species of R—$Si(OSi)_2(OH)$ and R—$Si(OSi)_3$. The $\Sigma T^n/\Sigma Q^m$ ratio, where n and m were 2-3 and 2-4, respectively, was around 0.066, closed to the elemental analysis. It also revealed that most of propylsulfonic acid groups was co-condensed on the silica framework of mesoporous silica materials.

III. Synthesis of Functionalized Mesoporous Silica Materials of Platelet Morphology and Short Mesochannels—with Prehydrolysis Organic functionalized mesoporous SBA-15 silica materials of platelet morphology and short mesochannels was also prepared by dissolving Pluronic P123 triblock copolymer (Aldrich, Mn=5800) in HCl solution at 35° C., followed by adding silicon source and adding a small amount of Zr(IV) ions to form a hydrolysis solution. After hydrolyzing silicon source for 1-4 h, organosilane was added into the hydrolysis solution to form a third synthesis solution. The third synthesis solution was sealed in a polypropylene bottle, stirred at 35° C. for 24 h, and then hydrothermally heated at 90° C. under static condition for another 24 h. The solid product was filtered, washed with de-ionized water and dried at 50° C. overnight. The P123 templates were then removed by ethanol extraction at 78° C. for 1 day.

EXAMPLE 9

Synthesis of —$(CH_2)_3NH_2$ Functionalized Mesoporous Silica Materials with Platelet Morphology and Short Mesochannels

TABLE 7

| Reactants | Molar ratio |
|---|---|
| P123 | 0.017 |
| TEOS | 1 |
| Amine containing silane* | 0.05-0.3 |
| Zr(IV) | 0.03-0.1 |
| HCl | 7.94 |
| NaCl | 0-3 |
| $H_2O$ | 221 |

*3-aminopropyltriethoxyl silane, or 3-aminopropyltrimethoxyl silane (APTMS)

In this example, —$(CH_2)_3NH_2$ functionalized mesoporous silica materials with platelet morphology and short mesochannels was synthesized. The reactant molar ratios are listed in Table 7. The Zr(IV) source was $ZrOCl_2.8H_2O$. In some caes, NaCl can be added into the synthesis gels in order to obtain highly-ordered pore structure.

FIG. 16A shows small-angle XRD patterns of aminopropyl-functionalized mesoporous silica materials prepared with various TEOS pre-hydrolysis (PT) times. In FIG. 16A, no diffraction peak is observed when aminopropyl-functionalized mesoporous silica material is prepared without TEOS pre-hydrolysis. When TEOS pre-hydrolysis is performed for 0.5-2 h, the resultant aminopropyl-functionalized mesoporous silica materials show an intense (100) diffraction peak and two weak (110) and (200) diffraction peaks corresponding to 2D-hexagonal p6mm pore structure.

Figure 16B:
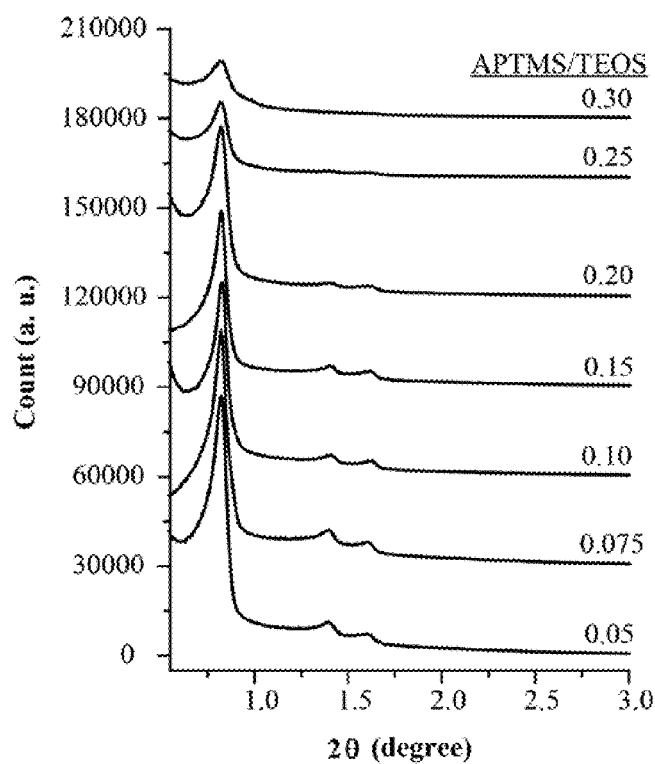
FIG. 16B shows small-angle XRD patterns of aminopropyl-functionalized mesoporous silica materials prepared with TEOS pre-hydrolysis time of 2 h and various APTMS/TEOS ratios.
Figure 17A:
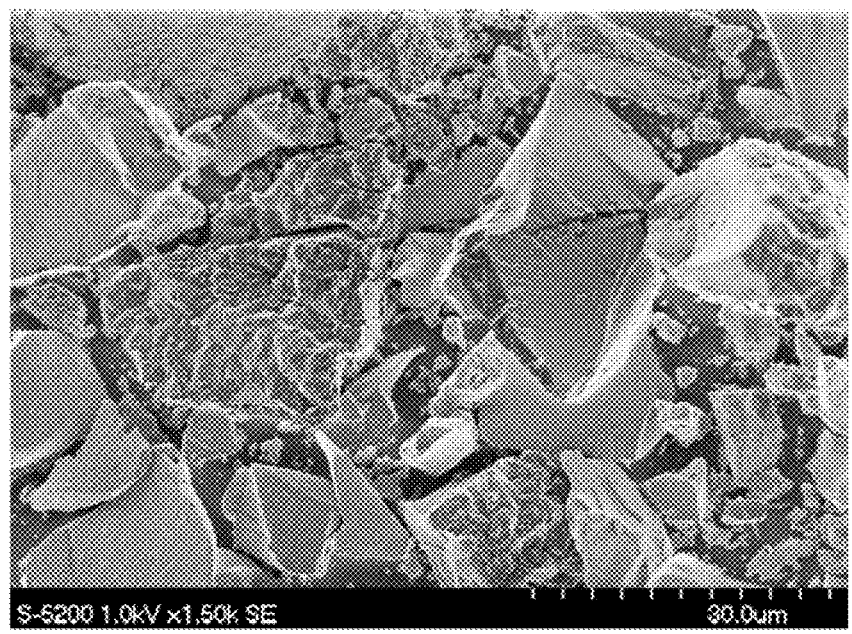
FIGS. 17A-17D show SEM and HR-SEM photographs of aminopropyl-functionalized mesoporous silica materials prepared with various TEOS pre-hydrolysis time of 0, 0.5, 2 h, and 2 h, respectively.
Figure 17B:
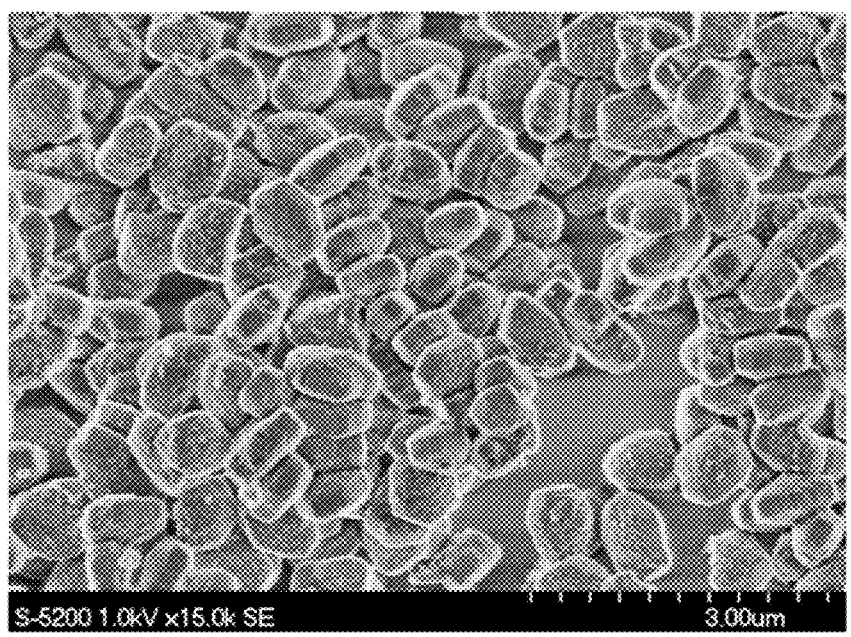
Figure 17C:
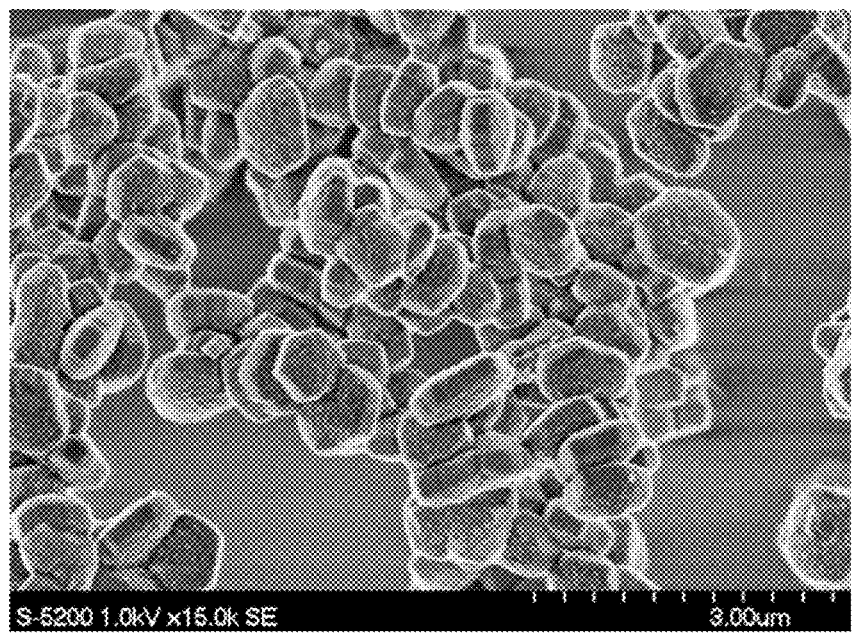
Figure 17D:
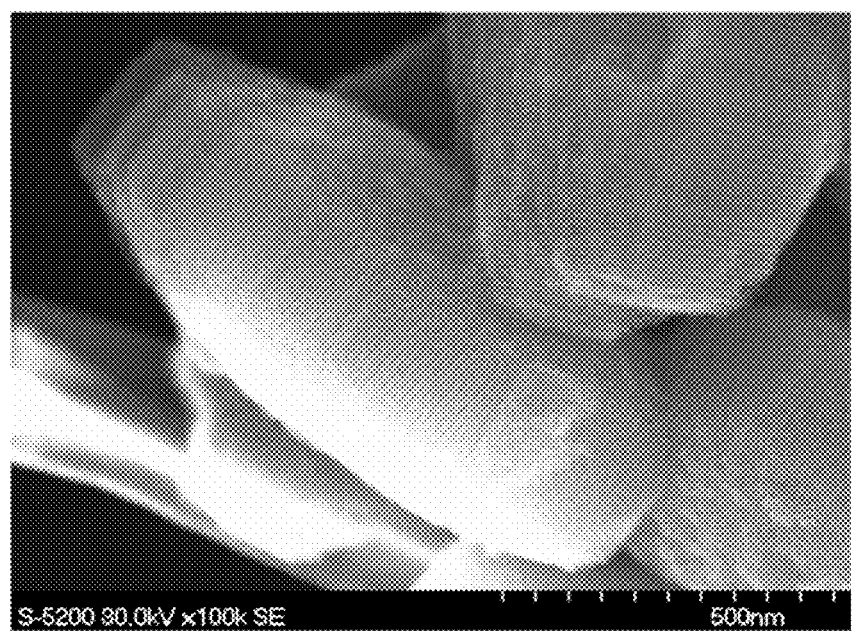

FIG. 16B shows small-angle XRD patterns of aminopropyl-functionalized mesoporous silica materials prepared with TEOS pre-hydrolysis time of 2 h and various APTMS/TEOS ratios. In FIG. 16B, (100), (110) and (200) diffraction planes of 2D hexagonal p6mm symmetry are found when aminopropyl-functionalized mesoporous silica materials are prepared by APTMS/TEOS ratios within 0.05-0.25. By further increasing the APTMS/TEOS ratio to 0.30, the XRD pattern of resultant material showed one broad and weak diffraction peak.

FIGS. 17A-17D show SEM and HR-SEM photographs of aminopropyl-functionalized mesoporous silica materials prepared with various TEOS pre-hydrolysis time of 0, 0.5, 2 h, and 2 h, respectively. The NaCl/Si in the gel is 2. In FIG. 17, the morphology of aminopropyl-functionalized mesoporous silica material prepared without TEOS pre-hydrolysis is large and irregular aggregates with sizes at micrometer level. When TEOS is pre-hydrolyzed for only 0.5-2 h, the morphology is dramatically changed to homogeneously dispersed hexagonal thin platelets with 900-1100 in width and 150-350 nm in thickness, respectively. The short mesochannels (150-350 nm) that have well-arranged into 2D-hexagonal p6mm symmetry are found in the platelet aminopropyl-functionalized mesoporous silica materials prepared with TEOS pre-hydrolysis times of 0.5-2 h.

Figure 18A:
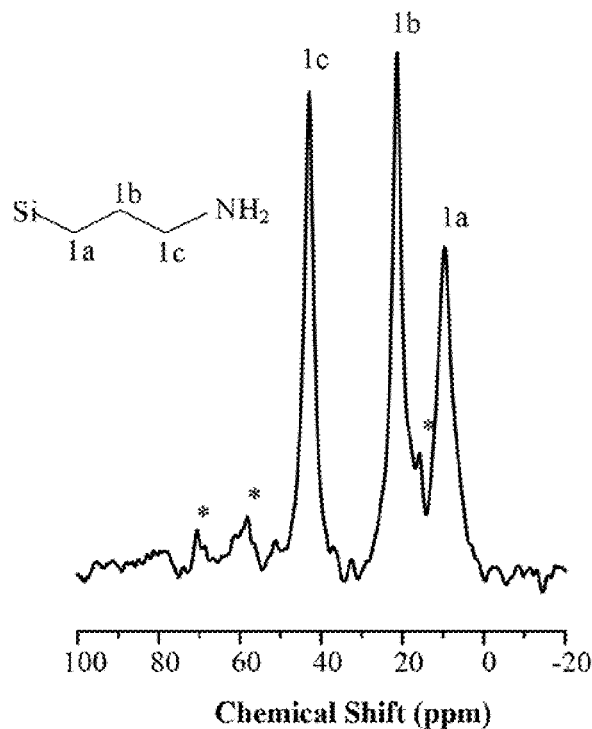
FIG. 18A shows solid state $^{13}C$ CP-MAS spectra of various extracted aminopropyl-functionalized mesoporous silica materials with platelet morphology and short mesochannels.

FIG. 18A shows solid state $^{13}C$ CP-MAS spectra of various extracted aminopropyl-functionalized mesoporous silica materials with platelet morphology and short mesochannels. Peaks labeled * corresponding to carbon atoms from the P123 residue. In FIG. 18A, $^{13}C$ CP-MAS NMR spectrum shows that three distinct peaks centered at 9.8, 21.3 and 43.1 ppm, corresponding to the carbon atoms on the ≡Si—$CH_2$—$CH_2$—$CH_2$—$NH_2$ group in the sequence from left to right, can be clearly observed. It indicates that APTMS is co-condensed as a part of silica framework without the decomposition of organic moieties during the synthesis.

Figure 18B:
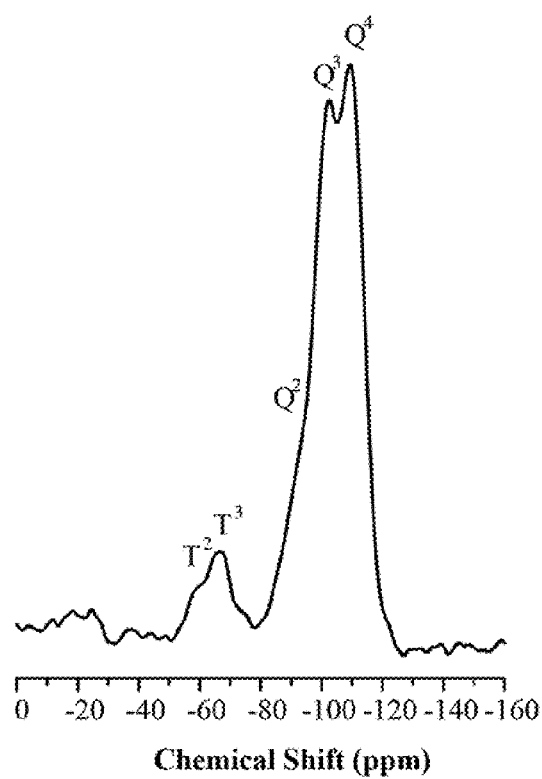
FIG. 18B shows $^9Si$ MAS NMR spectra of various extracted aminopropyl-functionalized mesoporous silica materials with platelet morphology and short mesochannels.

FIG. 18B shows $^9Si$ MAS NMR spectra of various extracted aminopropyl-functionalized mesoporous silica materials with platelet morphology and short mesochannels. In the $^{29}Si$ MAS NMR spectrum, three distinct resonance peaks with chemical shifts of −91, −102.2, −109.2 ppm are assigned as $Q^2$, $Q^3$ and $Q^4$ bands corresponding to the siloxanes species of $Si(OSi)_2(OH)_2$, $Si(OSi)_3(OH)$ and $Si(OSi)_4$. Another two resonance peaks are observed at −58 and −66 ppm, which are designated as the $T^2$ and $T^3$ bands corresponding to the organosiloxane species of R—$Si(OSi)_2(OH)$ and R—$Si(OSi)_3$. The $T^1$ band corresponding to the organosiloxane species of R—$Si(OSi)(OH)_2$ is not observed and the $T^3$ band is more intense than $T^2$ band. It indicates that APTMS is efficiently hydrolyzed and incorporated as a part of silica framework. The $\Sigma T^m/\Sigma Q^n$ value is around 0.080, which are in consistence with the results of elemental analyses.

EXAMPLE 10

Synthesis of Arene-sulfonic Acid-functionalized Mesoporous Silica Materials with Platelet Morphology and Short Mesochannels

TABLE 8

| Reactants | Molar ratio |
|---|---|
| P123 | 0.017 |
| Si* | 1 |
| CSPETES** | 0.01 |
| Zr(IV) | 0.05 |
| HCl | 7.94 |
| NaCl | 0-3 |
| $H_2O$ | 221 |

*TEOS or sodium silicate
**2-(4-Chlorosulfonyl-phenyl)ethyltriethoxysilane (50% solution in dichloromethane)

In this example, arene-sulfonic acid functionalized mesoporous silica materials with platelet morphology and short mesochannels was synthesized. The reactant molar ratios are listed in Table 8. The Zr(IV) source was $ZrOCl_2.8H_2O$. The pre-hydrolysis time is 2 h.

Figure 19A:
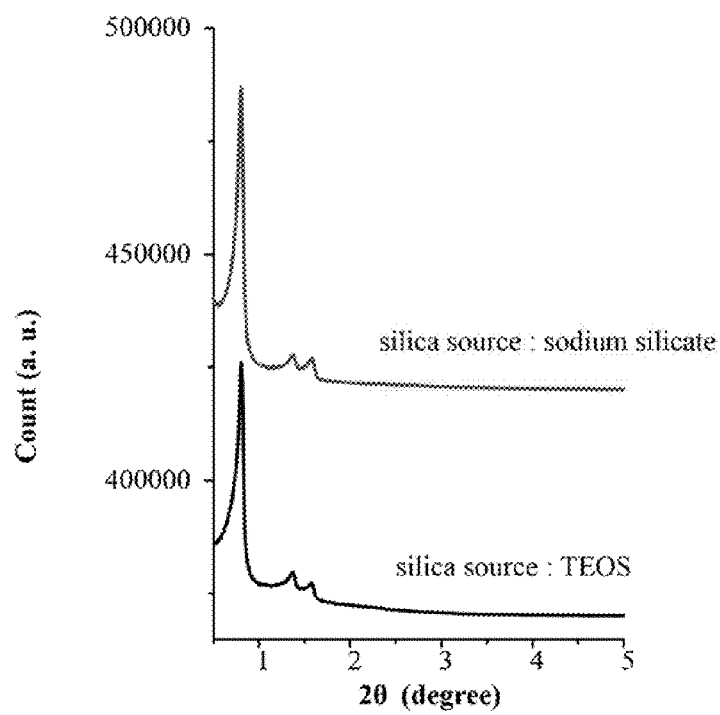
FIG. 19A shows small-angle XRD patterns of extracted arene-sulfonic acid-functionalized mesoporous silica materials with platelet morphology prepared by CPTES/TEOS and CPTES/sodium silicate.

FIG. 19A shows small-angle XRD patterns of extracted arene-sulfonic acid-functionalized mesoporous silica materials with platelet morphology prepared by CSPETES/TEOS and CSPETES/sodium silicate. In FIG. 19A, the arene-sulfonic acid-functionalized mesoporous silica materials prepared with either TEOS or sodium silicate as the silicon sources show similar (100), (110) and (200) diffraction planes of 2D hexagonal p6mm symmetry.

Figure 19B:
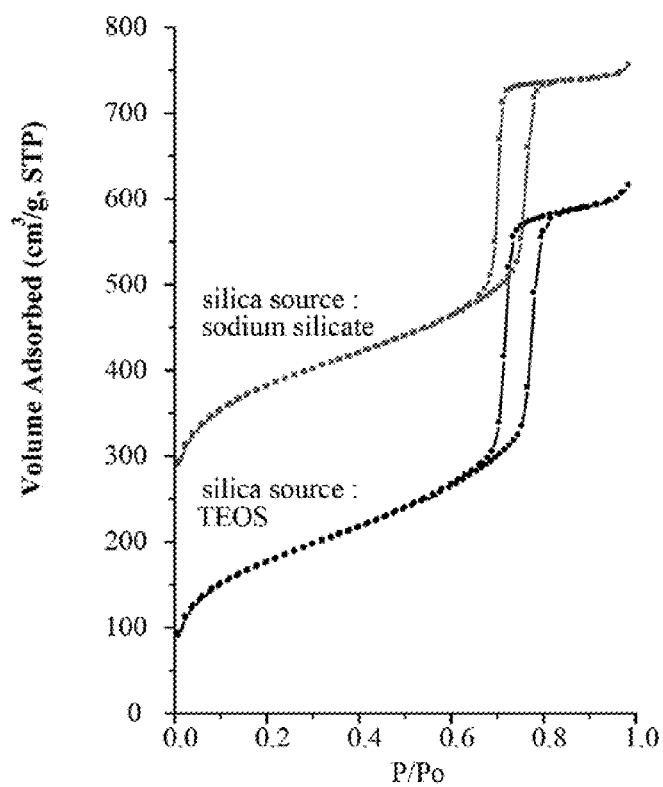
FIG. 19B shows $N_2$ adsorption-desorption isotherms of extracted arene-sulfonic acid-functionalized mesoporous silica materials with platelet morphology prepared by CSPETES/TEOS and CSPETES/sodium silicate.

FIG. 19B shows $N_2$ adsorption-desorption isotherms of extracted arene-sulfonic acid-functionalized mesoporous silica materials with platelet morphology prepared by CSPETES/TEOS and CSPETES/sodium silicate. N₂ adsorption-desorption isotherms and pore size distributions indicate that both materials prepared by one pot method contain large mesoporous structure with narrow PSD.

Figure 20A:
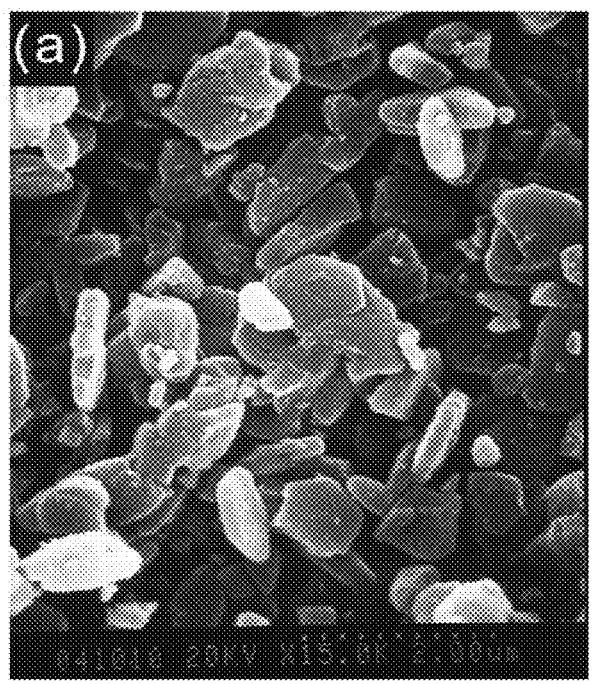
FIGS. 20A and 20B show SEM photographs of extracted arene-sulfonic acid-functionalized mesoporous silica materials with platelet morphology prepared by CSPETES/TEOS and CSPETES/sodium silicate, respectively.
Figure 20B:
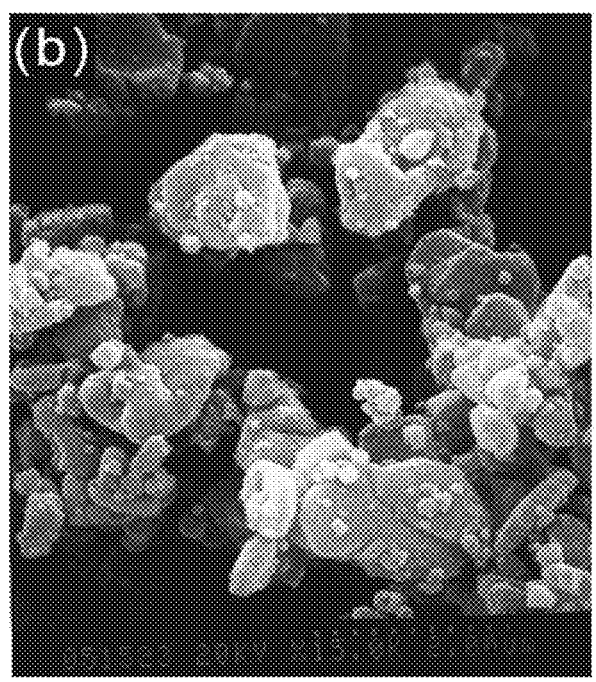

FIGS. 20A and 20B show SEM photographs of extracted arene-sulfonic acid-functionalized mesoporous silica materials with platelet morphology prepared by CSPETES/TEOS and CSPETES/sodium silicate, respectively. In FIGS. 20A and 20B, the SEM photographs show that both arene-sulfonic acid-functionalized mesoporous silica materials synthesized by CSPETES/TEOS and CSPETES/sodium silicate are platelet morphology and short mesochannels.

EXAMPLE 11

Synthesis of Carboxylic Acid-Functionalized Mesoporous Silica Materials with Platelet Morphology and Short Mesochannels

TABLE 9

| Reactants | Molar ratio |
| --- | --- |
| P123 | 0.017 |
| Si* | 1 |
| CPTES** | 0.1 |
| Zr(IV) | 0.05 |
| HCl | 7.94 |
| H₂O | 221 |

*TEOS or sodium silicate
**3-Cyanopropyltriethoxysilane

The platelet cyanoprpoyl-functionalized mesoporous silica material with short mesochannels was first prepared. Then, the cyano group was hydrolyzed to produce carboxylic acid group by refluxed in 6 M HCl for 1 d to obtain carboxylic acid-functionalized mesoporous silica materials. The reactant molar ratios are listed in Table 9. The Zr(IV) source was ZrOCl$_2$·8H$_2$O.

Figure 21A:
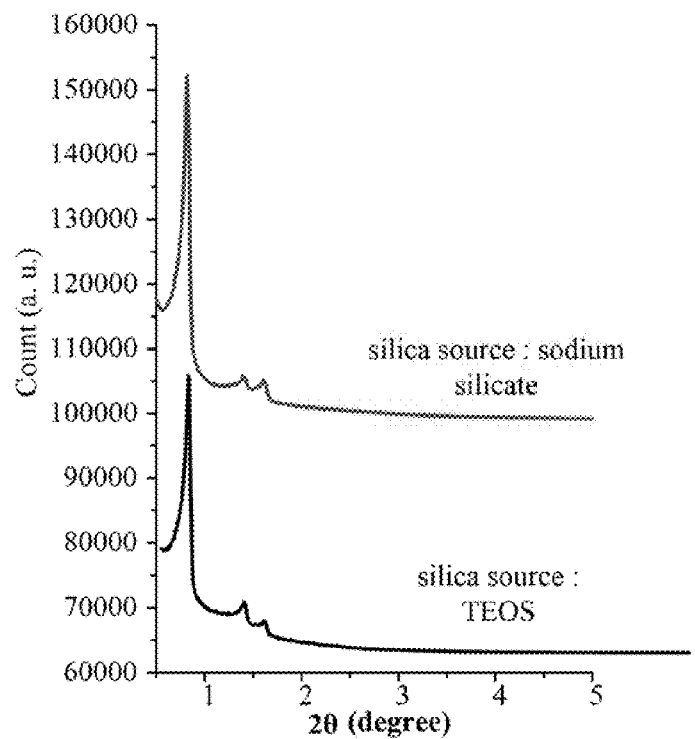
FIG. 21A is Small-angle XRD patterns of extracted carboxylic acid-functionalized mesoporous silica materials with platelet morphology prepared by CPTES/TEOS and CPTES/sodium silicate.

FIG. 21A is Small-angle XRD patterns of extracted carboxylic acid-functionalized mesoporous silica materials with platelet morphology is prepared by CPTES/TEOS and CPTES/sodium silicate. In FIG. 21A, the carboxylic acid-functionalized mesoporous silica materials prepared with either TEOS or sodium silicate as the silica sources show similar (100), (110) and (200) diffraction planes of 2D hexagonal p6mm symmetry.

Figure 21B:
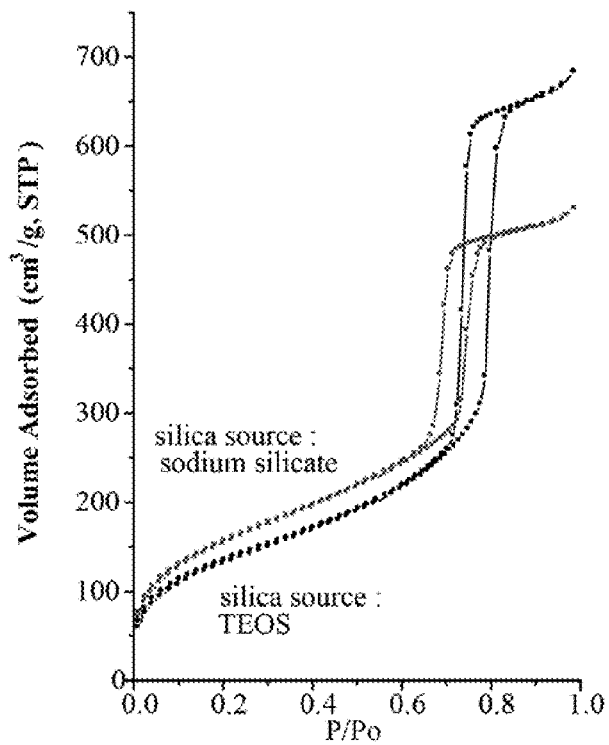
FIG. 21B is $N_2$ adsorption-desorption isotherms of extracted carboxylic acid-functionalized mesoporous silica materials with platelet morphology prepared by CPTES/TEOS and CPTES/sodium silicate.

FIG. 21B is N$_2$ adsorption-desorption isotherms of extracted carboxylic acid-functionalized mesoporous silica materials with platelet morphology prepared by CPTES/TEOS and CPTES/sodium silicate. In FIG. 21B, N$_2$ adsorption-desorption isotherms and pore size distributions indicate that both materials prepared by one pot method contain large mesoporous structure with narrow PSD.

Figure 22A:
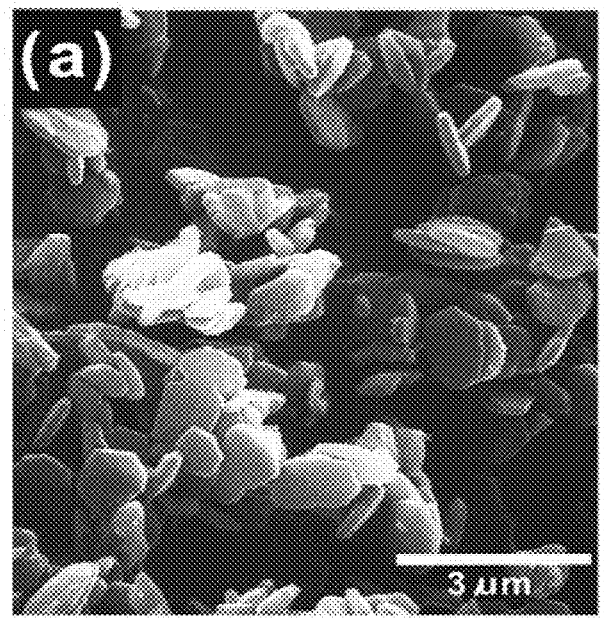
FIGS. 22A-22B show the SEM photographs of extracted carboxylic acid-functionalized mesoporous silica materials with platelet morphology prepared by CPTES/TEOS and CPTES/sodium silicate, respectively.
Figure 22B:
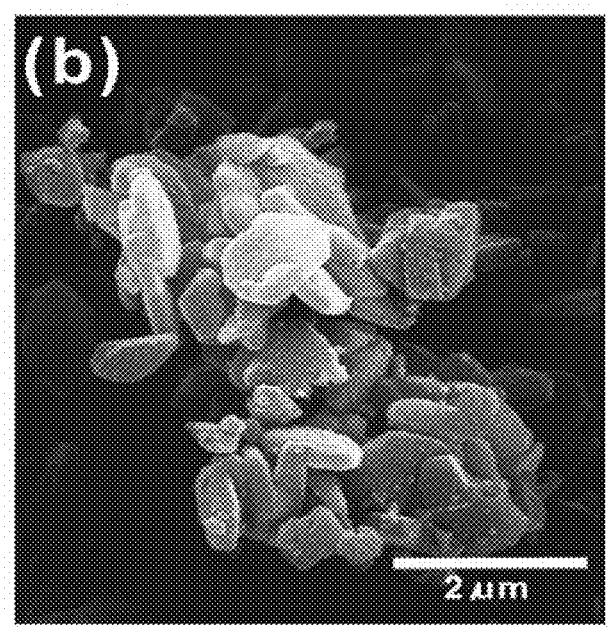

FIGS. 22A-22B show the SEM photographs of extracted carboxylic acid-functionalized mesoporous silica materials with platelet morphology prepared by CPTES/TEOS and CPTES/sodium silicate, respectively. In FIG. 22, the SEM photographs show that both carboxylic acid-functionalized mesoporous silica materials with CPTES/TEOS and CPTES/sodium silicate are platelet morphology and short mesochannels.

IV. Uptakes of Organic Molecules by Organic-functionalized Mesoporous is Silica Materials with Platelet and Fiber Morphologies The organic-functionalized mesoporous silica materials with platelet morphology were synthesized by the method with or without prehydrolysis, as described above, and hence omitted here. The organic-functionalized mesoporous silica materials with fiber morphology were synthesized by conventional method, i.e. without adding Zr(IV) ions at all.

EXAMPLE 12

Uptakes of New Coccine Dye and Octadecane

The uptakes of new coccine dye (see Formula I) and octadecane on organic-functionalized mesoporous silica materials with platelet and fiber morphologies are compared and summarized in Table 10. The adsorption experiments were carried out at RT for 1 day. New coccine was dissolved in ethanol, and octadecane was dissolved in hexane.

TABLE 10

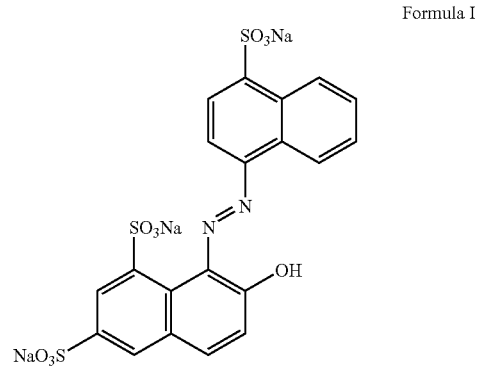

Formula I

|  | Uptake of new coccine (mmol/g) | | Uptake of octadecane (mmol/g) | |
| --- | --- | --- | --- | --- |
| Functionality | Long meso-channels | Short meso-channels | Long meso-channels | Short meso-channels |
| None | 0.34 | 0.37 | 0.40 | 1.10 |
| —CH₃ | 0.65 | 0.93 | 7.83 | 8.04 |
| —Ph | 0.71 | 1.18 | 5.90 | 7.69 |
| —(CH₂)₃Cl | 0.73 | 0.93 | 5.00 | 7.77 |
| —(CH₂)₃SH | 1.11 | 1.35 | 5.49 | 6.19 |
| —(CH₂)₃NH₂ | 14.3 | 15.4 | 2.44 | 5.25 |
| —(CH₂)₃CN | 0.77 | 1.23 | 5.00 | 5.75 |

Table 10 shows adsorption amounts of new coccine and octadecane over extracted organic functionalized mesoporous silica materials with short and long mesochannels. The uptakes of new coccine on conventional mesoporous silica materials are all slightly lower than those over platelet materials. The differences are enlarged when the materials contain organic functional groups, especially phenyl and cyanopropyl groups. It is also noticeable that the absorption capacities of aminopropyl-functionalized mesoporous silica materials toward new coccine are much higher than those over other materials, probably due to the strong hydrogen-bond interaction between the anchored aminopropyl and the sulfate groups on the dye.

Figure 23:
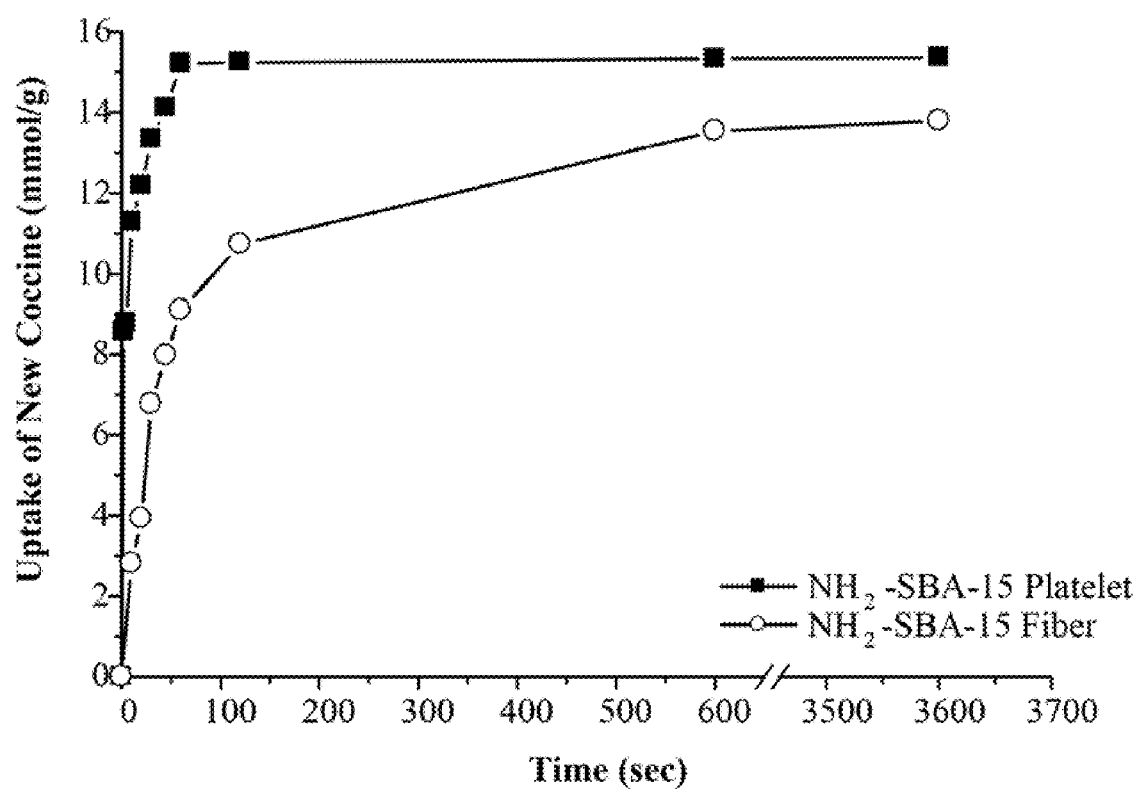
FIG. 23 shows the uptakes of new coccine as a function of adsorption period at RT over extracted $NH_2(CH_2)_3$-functionalized mesoporous silica materials with short (■) and long (○) mesochannels.

The adsorption rates of new coccine dye on aminopropyl-functionalized s mesoporous silica materials with short and long mesochannels were compared in order to understand the effect of pore length on the molecular diffusivity through the channels. FIG. 23 shows the uptakes of new coccine as a function of adsorption period at RT over extracted $NH_2(CH_2)_3$-functionalized mesoporous silica materials with short (■) and long (○) mesochannels. In FIG. 23, it takes ca. 10 min for the adsorption of new coccine dye to reach equilibrium on the fiber material, while it takes only 1 min on the platelet material.

These results demonstrate that the short mesochannels facilitate the diffusion of the bulky dye molecules through the channels. Moreover, the higher uptake of new coccine dye by mesoporous silica material with platelet morphology and short mesochannels is attributed to the less possibility of pore-blockage in comparison to that with long mesochannels.

V. Reactions Catalyzed by Organic Functionalized-Mesoporous Silica Materials of Platelet Morphology and Short Mesochannels

EXAMPLE 13

Organic Functionalized-Mesoporous Silica Materials used as Solid Base

When the amine groups are incorporated into the mesoporous silica materials with platelet morphology and short mesochannels, it is an efficient solid base catalyst for many base-catalyzed reactions, such as Michael additions, Knoevenagel condensations, nitroaldol condensation and flavanone synthesis.

Flavaone synthesis was tested. Flavaone can be synthesized by condensation of benzaldehyde and 2'-hydroxyacetophenone and subsequent intramolecular Michael addition of 2'-hydroxychalcone, as shown in Eq. (1).

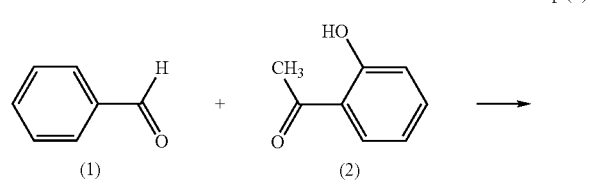

Eq. (1)

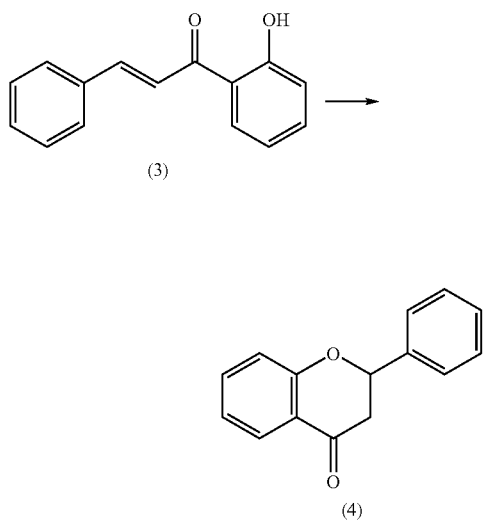

Figure 24:
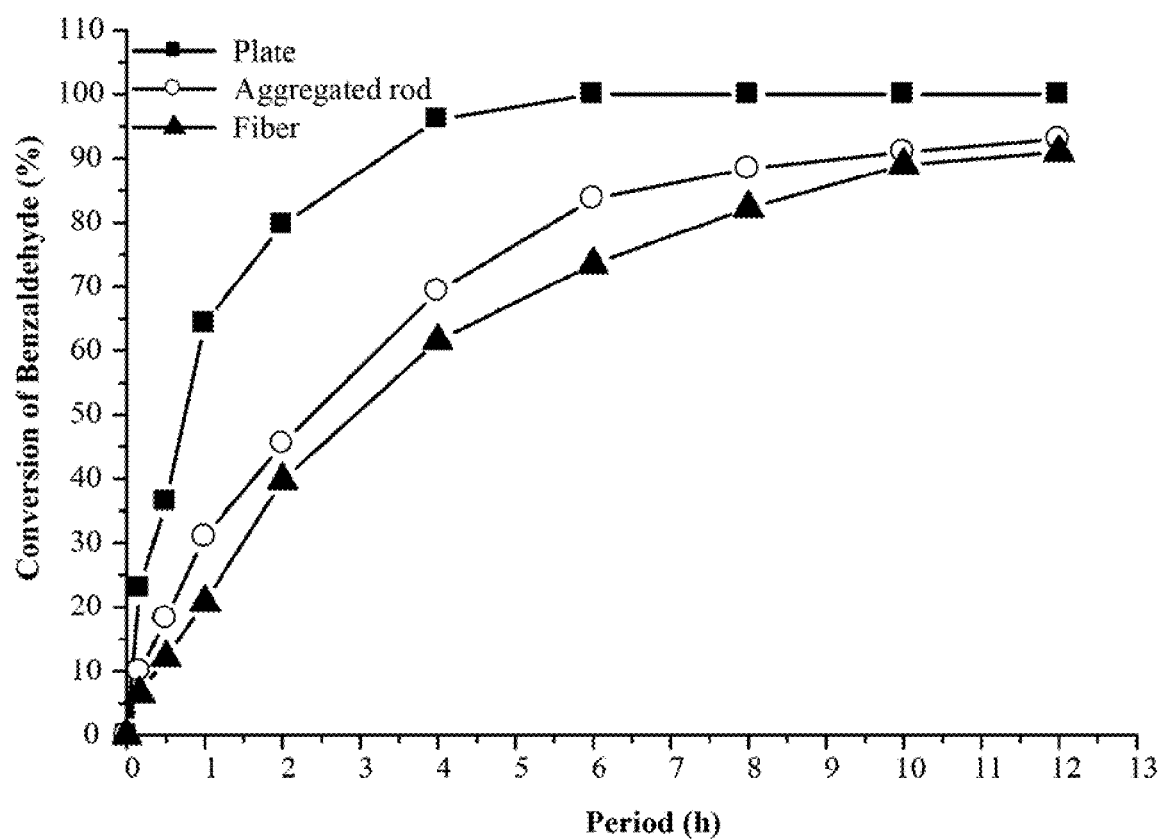
FIG. 24 shows benzaldehyde conversion over amine-based functionalized mesoporous silica materials prepared with plate (■), aggregated plate (○), and fiber (▲) morphologies as a function of reaction time.

FIG. 24 shows benzaldehyde conversion over amine-based functionalized mesoporous silica materials prepared with plate (■), aggregated plate (○), and fiber (▲) morphologies as a function of reaction time. These amine-based functionalized mesoporous silica materials with various morphologies were synthesized with various NaCl/TEOS ratios (y in Table 11 below). The condensation reactions were performed at 140° C. without solvent.

For amine-functionalized mesoporous silica material with platelet morphology and short mesochannels, the benzaldehyde conversion is quickly is and linearly raised in the beginning of 1 h and then slows down by further prolonging the reaction period. The flavanone yield is progressively increased with reaction period and reaches about 72% at equilibrium. The benzaldehyde conversions over aggregated rodlike or fiberlike aminopropyl-functionalized mesoporous silica materials with long mesochannels at the micrometer level are slowly increased to 90% by prolonging the reaction period to for 10 h. At this time, the flavanone yield is around 60%, which is lower than that over platelet aminopropyl-functionalized mesoporous silica material with short mesochannels at similar reaction period.

TABLE 11

| y | Morphology | Mesochannels length (nm) | $S_{BET}$ (m$^2$/g) | $V_{Total}$ (cm$^3$/g) | $\Phi_P$* (nm) | Conv. (%) (1)** | Yield (%) (3)** | Yield (%) (4)** | TON (h$^{-1}$) |
|---|---|---|---|---|---|---|---|---|---|
| 2 | Platelets | 150-350 | 442 | 0.74 | 6.5 | 96.1 | 27.3 | 49.2 | 8.75 |
| 3.5 | Aggregated rods | ↓ | 429 | 0.80 | 6.4 | 69.3 | 25.9 | 22 | 5.93 |
| 6 | Fiber | >10,000 | 446 | 0.74 | 6.3 | 61.6 | 22.6 | 18.1 | 5.08 |

*Pore size.
**Please see Eq (1).

Table 11 shows the structural property and catalytic activities of TMAOH-treated amine-functionalized mesoporous silica materials prepared with various NaCl/TEOS ratios (y), and their catalytic performances in the condensation of benzaldehyde and 2'-hydroxyacetophenone without solvent at 140° C. for 4 h. As shown in Table 11, the turnover number for platelet aminopropyl-functionalized mesoporous silica material with short mesochannel is 8.75 h$^{-1}$, which is much higher than that of aggregated rodlike or fiberlike aminopropyl-functionalized mesoporous silica materials with long mesochannels (TON=5.08-5.93 h$^{-1}$). The result clearly indicates that Claisen-Schimdt condensation of benzaldehyde and 2'-hydroxyacetophenone and subsequent intramolecular Michael addition of 2'-hydroxychalcone to flavanone over aminopropyl-functionalized mesoporous silica material can be facilitated by increase of molecular diffusion through the shortened channeling pores.

EXAMPLE 14

Organic Functionalized-mesoporous Silica Materials used as Solid Acid

When the sulfonic acid groups are incorporated into mesoporous silica materials with platelet morphology and short mesochannels, it is an efficient s solid acid catalyst for many acid-catalyzed reactions, such as Bisphenol-A synthesis, esterification, alcohol coupling to ether, condensation and addition reaction, and esterification and trans-esterification.

Figure 25:
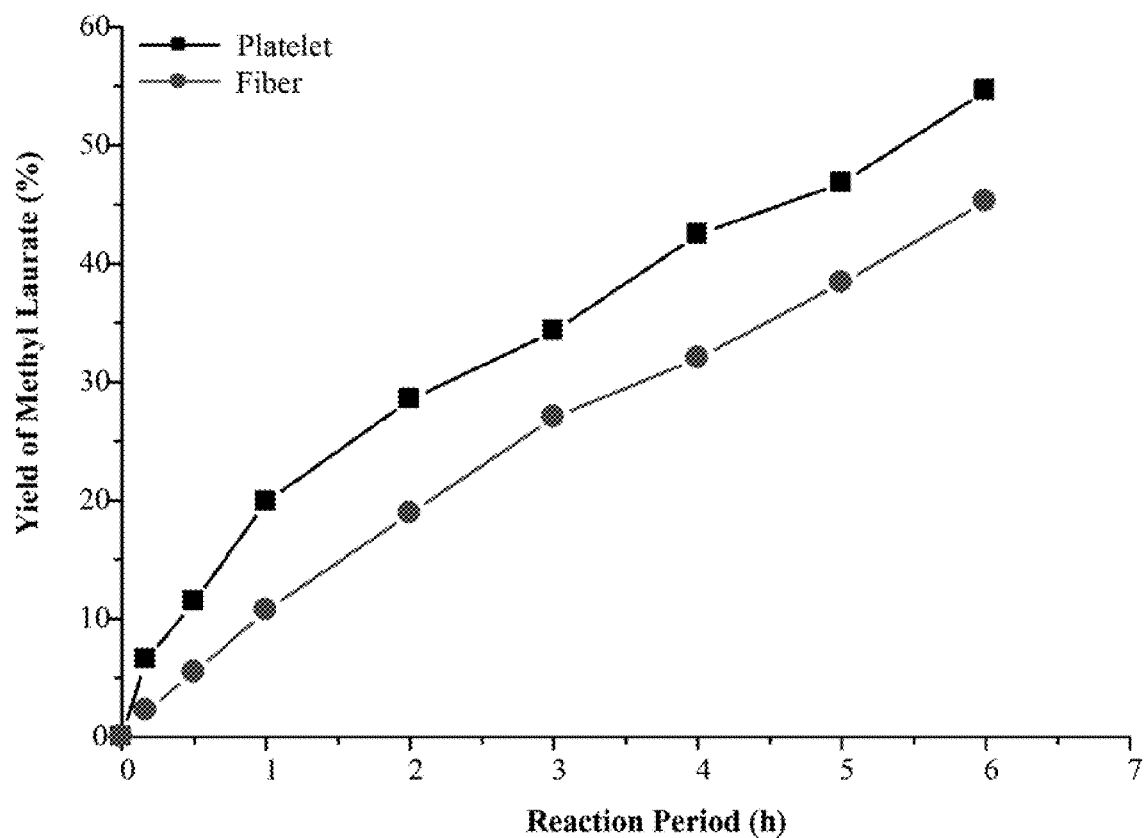
FIG. 25 shows the esterification of palimitic acid with methanol over propylsulfonic acid-functionalized mesoporous silica materials with short (■) and long (●) mesochannels.

The esterification of palimitic acid with methanol was test. FIG. 25 shows the esterification of palimitic acid with methanol over propylsulfonic acid-functionalized mesoporous silica materials with short (■) and long (●) mesochannels. It is clearly shown that the esterification of palimitic acid and methanol over sulfonic acid-functionalized mesoporous silica material with short mesochannels can be carried out more quickly than that with long mesochannels. The result indicates that the molecular diffusion through the channeling pores of mesoporous silica materials can be facilitated by shortening the channeling pores. As a result, the high yield of methyl palimitate is obtained over sulfonic acid-functionalized mesoporous silica materials with short mesochannels in a short reaction period, compared with conventional sulfonic acid-functionalized mesoporous silica materials with long mesochannele.

Figure 26:
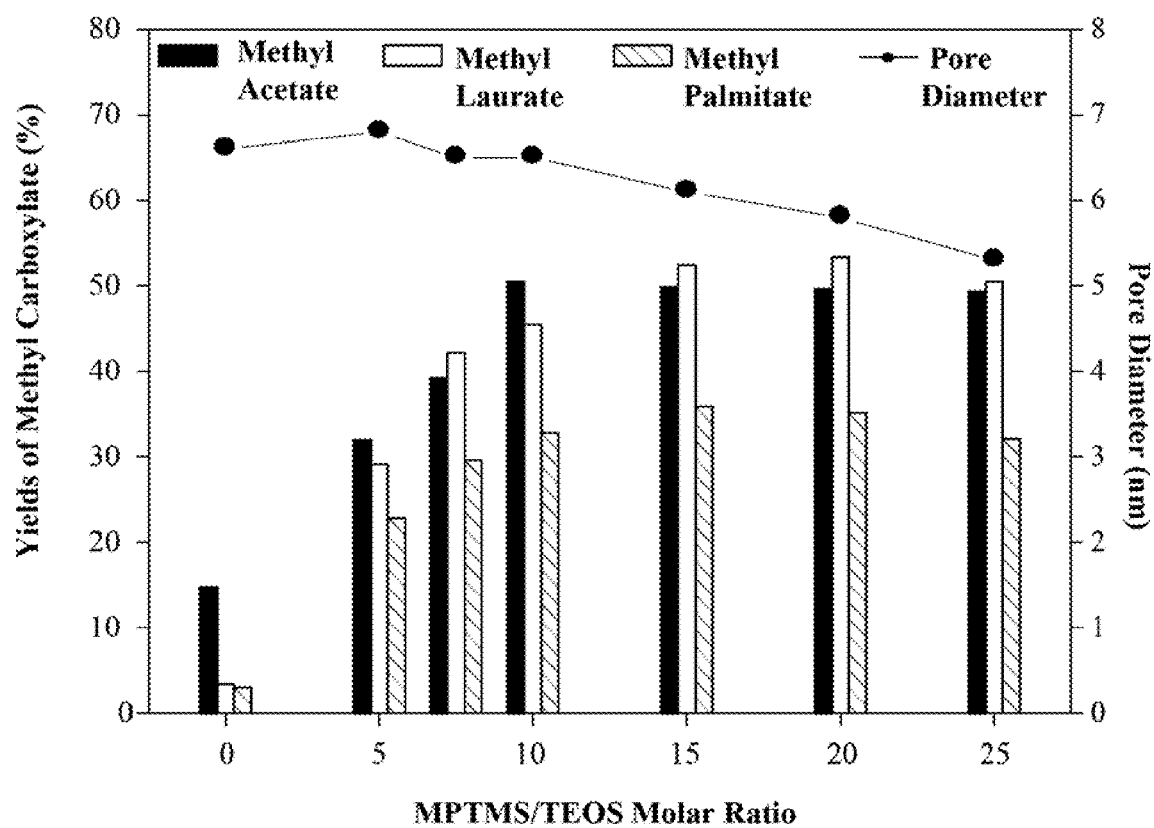
FIG. 26 shows the effect of sulfonic acid loadings on catalytic activity of conventional mesoporous silica material, and propylsulfonic acid-functionalized mesoporous silica materials with short mesochannels in esterification of carboxylic acids with methanol.

FIG. 26 shows the effect of sulfonic acid loadings on catalytic activity of conventional mesoporous silica material, and propylsulfonic acid-functionalized mesoporous silica materials with short mesochannels in esterification of carboxylic acids with methanol. Although esterification of carboxylic acid and methanol can be carried out over conventional mesoporous silica material, the methyl carboxylate yields are low. The methyl carboxylate yields can be obviously enhanced by incorporation of propylsulfonic acid griups on mesoporous silica materials. The propylsulfonic acid-functionalized mesoporous silica materials with platelet morphology and short mesochannels prepared with MPTMS/TEOS ratios of 0.10-0.20 display highest catalytic activity in esterification of carboxylic acids and methanol.

Accordingly, a facile synthesis route for preparing SBA-15 silica of platelet shape and very short mesochannels (150-350 nm) was developed by introducing a small amount of Zr(IV) ions in the synthesis solution. The synthesis route can be easily extended to prepare SBA-15 materials with various organic functional groups up to 1.87 mmol/g loading in one pot. The platelet SBA-15 materials are superior to the conventional SBA-15 of rod or fiber morphologies in facilitating molecular diffusion and less possibility of pore blockage when used in the sorption or reactions of bulky molecules.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method of forming an organic-functionalized and zirconium doped mesoporous silica with platelet morphology and short mesochannels having a channel length of about 100-350 nm, comprising:
    adding $EO_{20}PO_{70}EO_{20}$, silicon source, organosilane and Zr(IV) ions into a HCl solution to form a synthesis solution, wherein the molar ratio of $EO_{20}PO_{70}EO_{20}$, silicon source, organosilane, Zr(IV) ions, HCl and $H_2O$ is 0.008-0.02:1:0.05-0.3:0.03-0.1:4-12:100-310;
    hydrothermally heating the synthesis solution to form the mesoporous silica; and
    removing $EO_{20}PO_{70}EO_{20}$ from the pores of the mesoporous silica.

2. The method of claim 1, wherein the silicon source is tetraethyl orthosilicate (TEOS) or sodium silicate.

3. The method of claim 1, wherein the organosilane is trialkoxy silane or trihalide silane.

4. The method of claim 1, wherein the organosilane is methyltriethoxysilane, phenyltriethoxysilane, (3-chloropropyl)trimethoxysilane, 3-mercaptopropyl-trimethoxysilane, 3-aminopropyltrimethoxysilane, 3-cyanopropyltriethoxysilane, 2-(4-chlorosulfonylphenyl)ethyltrimethoxysilane or carboxyethylsilanetriol sodium salt.

5. The method of claim 1, wherein the Zr(IV) ions are provided by $ZrOCl_2$, $ZrO(NO_3)_2$, and zirconium(IV) acetate hydroxide.

6. The method of claim 1, wherein the molar ratio of $EO_{20}PO_{70}EO_{20}$, silicon source, organosilane, Zr(IV) ions, HCl and $H_2O$ is 0.008-0.02:1:0.05-0.3:0.03-0.1:7-9:179-230.

7. The method of claim 1, further comprising adding a salt into the HCl solution and the molar ratio of salt/silicon source is not greater than 2.

8. The method of claim 7, wherein the salt is LiCl, LiBr, NaCl, NaBr, KCl, or KBr.

9. The method of claim 1, wherein the synthesis solution is hydrothermally heated at 90° C. under static condition for 24 h.

10. The method of claim 1, wherein the $EO_{20}PO_{70}EO_{20}$ is removed by solvent extraction at 78° C. for 1 day.

11. An organic-functionalized and zirconium-doped mesoporous silica with hexagonal platelet morphology and short mesochannels having a channel length of about 100-350 nm formed by the following steps comprising:
    adding $EO_{20}PO_{70}EO_{20}$, silicon source, organosilane and Zr(IV) ions into a HCl solution to form a synthesis solution, wherein the molar ratio of $EO_{20}PO_{70}EO_{20}$, silicon source, organosilane, Zr(IV) ions, HCl and $H_2O$ is 0.008-0.02:1:0.05-0.3:0.03-0.1:4-12:100-310;
    hydrothermally heating the synthesis solution to form the mesoporous silica; and
    removing $EO_{20}PO_{70}EO_{20}$ from the pores of the mesoporous silica.

12. The mesoporous silica of claim 11, wherein the silicon source is tetraethyl orthosilicate (TEOS) or sodium silicate.

13. The mesoporous silica of claim 11, wherein the organosilane is trialkoxy silane or trihalide silane.

14. The mesoporous silica of claim 11, wherein the organosilane is methyltriethoxysilane, phenyltriethoxysilane, (3-chloropropyl)trimethoxysilane, 3-mercaptopropyl-trimethoxysilane, 3-aminopropyltrimethoxysilane, 3-cyanopropyltriethoxysilane, 2-(4-chlorosulfonylphenyl)ethyltrimethoxysilane or carboxyethylsilanetriol sodium salt.

15. The mesoporous silica of claim 11, wherein the Zr(IV) ions are provided by $ZrOCl_2$, $ZrO(NO_3)_2$, and zirconium(IV) acetate hydroxide.

16. The mesoporous silica of claim 11, wherein the molar ratio of $EO_{20}PO_{70}EO_{20}$, silicon source, organosilane, Zr(IV) ions, HCl and $H_2O$ is 0.008-0.02:1:0.05-0.3:0.03-0.1:7-9:179-230.

17. The mesoporous silica of claim 11, further comprising adding a salt into the HCl solution and the molar ratio of salt/silicon source is not greater than 2.

18. The mesoporous silica of claim 17, wherein the salt is LiCl, LiBr, NaCl, NaBr, KCl, or KBr.

19. An organic-functionalized and zirconium-doped mesoporous silica with hexagonal platelet morphology and short mesochannels having a channel length of about 100-350 nm, wherein a loading of an organic functional group is not greater than 0.3 mol/mol $SiO_2$.

20. The mesoporous silica of claim 19, wherein the organic functional group is methyl, phenyl, 3-chloropropyl, 3-mercaptopropyl, 3-aminopropyl, 3-cyanopropyl, 2-(4-chlorosulfonylphenyl), carboxyethyl.

* * * * *